(12) United States Patent
El-Eskandarany et al.

(10) Patent No.: US 9,609,874 B1
(45) Date of Patent: Apr. 4, 2017

(54) METALLIC GLASSY ALLOY POWDERS FOR ANTIBACTERIAL COATING

(71) Applicant: KUWAIT INSTITUTE FOR SCIENTIFIC RESEARCH, Safat (KW)

(72) Inventors: Mohamed Sherif Mohamed Mostafa El-Eskandarany, Safat (KW); Ahmed Salem Abdulhadi Aldamier Al-Azmi, Aldasma (KW)

( * ) Notice: Subject to any disclaimer, the term of this patent is extended or adjusted under 35 U.S.C. 154(b) by 0 days.

(21) Appl. No.: 15/216,678

(22) Filed: Jul. 21, 2016

(51) Int. Cl.
| | |
|---|---|
| C23C 24/04 | (2006.01) |
| A01N 59/20 | (2006.01) |
| B22F 9/04 | (2006.01) |
| C22C 45/00 | (2006.01) |
| A01N 25/12 | (2006.01) |
| A01N 59/16 | (2006.01) |
| A61L 31/08 | (2006.01) |
| A61L 31/16 | (2006.01) |
| C09D 1/00 | (2006.01) |
| C09D 5/14 | (2006.01) |
| C09D 5/16 | (2006.01) |

(52) U.S. Cl.
CPC ............. *A01N 59/20* (2013.01); *A01N 25/12* (2013.01); *A01N 59/16* (2013.01); *A61L 31/088* (2013.01); *A61L 31/16* (2013.01); *B22F 9/04* (2013.01); *C09D 1/00* (2013.01); *C09D 5/14* (2013.01); *C09D 5/16* (2013.01); *C22C 45/001* (2013.01); *C23C 24/04* (2013.01); *A61L 2300/102* (2013.01); *A61L 2300/404* (2013.01); *A61L 2300/606* (2013.01); *B22F 2009/043* (2013.01)

(58) Field of Classification Search
USPC ................................................. 427/180, 383.1
See application file for complete search history.

(56) References Cited

U.S. PATENT DOCUMENTS

| | | | | |
|---|---|---|---|---|
| 8,574,615 | B2* | 11/2013 | Tenney | A61F 2/30767 424/423 |
| 8,802,191 | B2* | 8/2014 | Zimmermann | C23C 4/06 427/190 |
| 9,011,890 | B2 | 4/2015 | Wang et al. | |
| 2011/0293742 | A1 | 12/2011 | Yang | |
| 2012/0055783 | A1* | 3/2012 | Billieres | B22F 3/115 204/192.1 |
| 2012/0225312 | A1* | 9/2012 | Chin | A61L 2/232 428/553 |

* cited by examiner

*Primary Examiner* — Alexander Weddle
(74) *Attorney, Agent, or Firm* — Richard C. Litman

(57) ABSTRACT

The metallic glassy alloy powders for antibacterial coating are mechanically alloyed mixtures of copper, titanium, and nickel nanoparticles. The nanoparticles are alloyed by ball-milling to form glassy, metallic powders. The alloy preferably has a copper:titanium:nickel atomic percentage ratio of about 50:20:30, referred to herein as $Cu_{50}Ti_{20}Ni_{30}$. The powdered alloy is applied to a suitable substrate, such as stainless steel medical instruments, by cold spray powder coating. The coated substrate exhibits antibacterial properties compared to an uncoated substrate.

8 Claims, 25 Drawing Sheets

METALLIC GLASSY ALLOY POWDERS FOR ANTIBACTERIAL COATING

BACKGROUND OF THE INVENTION

1. Field of the Invention

The present invention relates to surface protective coatings, and particularly, to metallic glassy alloy powders for antibacterial coating made from metallic, glassy $Cu_{50}Ti_{20}Ni_{30}$ alloy nano-powders that are applied using a cold-spraying process.

2. Description of the Related Art

Surface protective coatings, which provide protection against corrosion and erosion and isolate the structural materials from chemical and physical interaction with the environment, is one of the vital applications of mechanically alloyed powders. Thermal spray and high velocity thermal spray coatings have been widely used in many vital applications, especially in the automotive aircraft industries. Unfortunately, thermal spray technology is not a proper process used for coating the desired bulk surfaces with metastable materials. This is attributed to the fact that thermal spray coating is not a solid-state process, since the coating materials are deposited on the surface of the substrate in a molten or semi-molten state to tailor the desired coat. Accordingly, it is expected that during the process, the feedstock metastable powders will suffer from crystallization and grain growth. Thus, all of the unique properties present in the original metastable powders would be absent after the coating process.

Most of the tools used in the medical and food sectors are made of austenitic stainless steel alloys (SUS316 and SUS304), which contain a high chromium content in the range between 12-20%. It is well established that using chromium metal as an alloying element in steel alloys greatly enhances the corrosion performance of such a traditional alloy. Although they have high corrosion resistance, SUS316 and SUS304 alloys do not possess antibacterial properties. Thus, infection and inflammation, which are usually promoted by adherence and colonization of bacteria onto the surfaces of stainless steel biomaterials, can be expected. Such a serious problem associated with bacterial adhesion may lead to significant complications resulting in a degradation of health, with many outcomes that may directly or indirectly affect human health.

The formation of biofilms in food products or food contact surfaces leads to severe problems with regards to hygienic standards and economic losses because of food spoilage. A new horizon related to the employing of nanoparticles as antimicrobials and antibacterial agents in the area of in the food industry has shown promising results on the capability of different types of fine powders (e.g., Ag, Au, Cu, CuO, MgO, $Al_2O_3$, TiO2, ZnO) to kill and resist agglomerations of many types of bacteria. A TiN coating also showed attractive results related to significant reduction of bacterial adhesion to the surface of a $Ti_6Al_4V$ substrate. It would be desirable to apply the principles of nanotechnology to synthesize a new antibacterial surface protective metallic alloy coating material.

Thus, metallic glassy alloy powders for antibacterial coating solving the aforementioned problems is desired.

SUMMARY OF THE INVENTION

The metallic glassy alloy powders for antibacterial coating are mechanically alloyed mixtures of copper, titanium, and nickel nanoparticles. The nanoparticles are alloyed by ball-milling to form glassy, metallic powders. The alloy preferably has a copper:titanium:nickel atomic percentage ratio of about 50:20:30, referred to herein as $Cu_{50}Ti_{20}Ni_{30}$. The powdered alloy is applied to a suitable substrate, such as stainless steel medical instruments, by cold spray powder coating. The coated substrate exhibits antibacterial properties compared to an uncoated substrate.

A method for synthesizing metallic alloy glassy powders includes the steps of disposing metal powders (copper, titanium, and nickel) in a ball milling container, the ball milling container including a plurality of milling balls and having an inert atmosphere therein; disposing the ball milling container including the metal powders in a ball mill; and operating the ball mill for a period of time to achieve high-energy collision of the plurality of balls with the metal powders in the container, the high energy collision producing a glassy metallic alloy powder.

A method for coating a substrate with metallic glassy powder includes the steps of providing a dry substrate having a surface to be coated; charging the metallic glassy powders obtained from the above process in a cold spray feeder; spraying the metallic glassy powders on to the surface in a supersonic jet of inert gas at a flow velocity of at least 1200 m/s, thereby coating the surface of the substrate with the metallic glassy powder. The coating has a uniform thickness.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
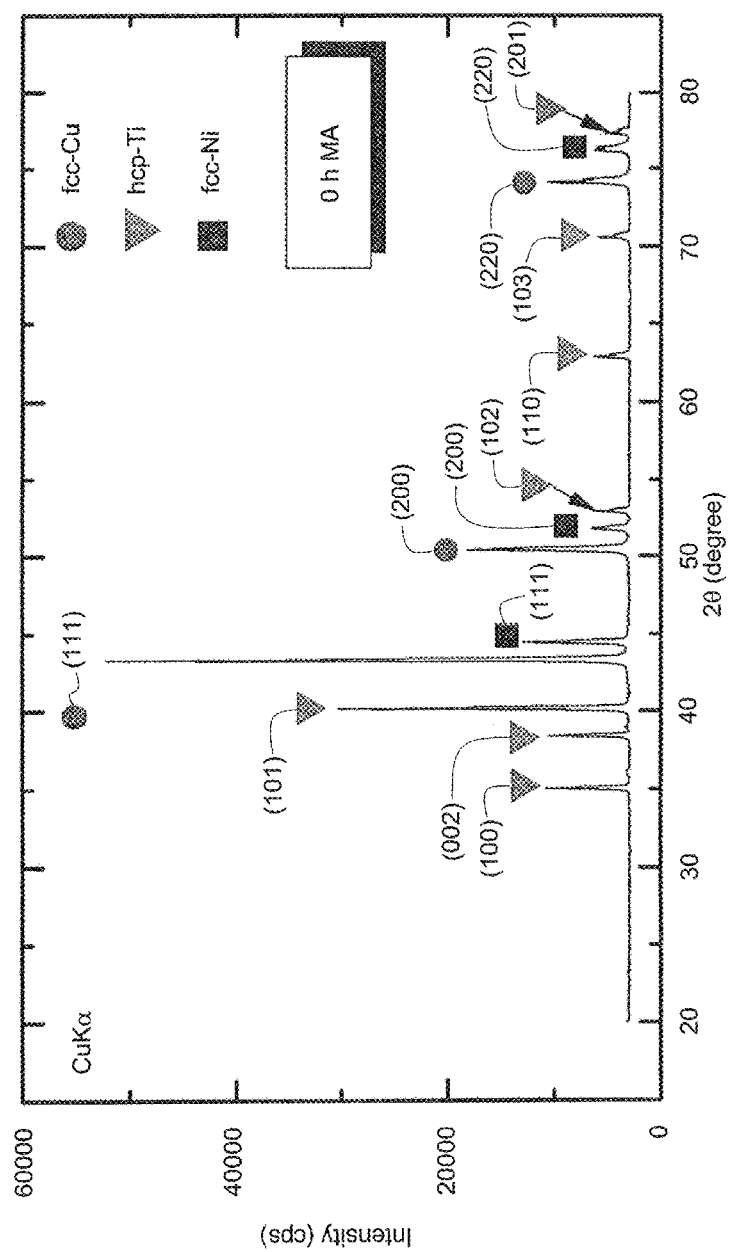
FIGS. 1A, 1B, and 1C are the X-ray diffraction (XRD) spectra of mechanically alloyed $Cu_{50}Ti_{20}Ni_{30}$ powders obtained after 0 h, 50 h, and 100 h, respectively, of ball milling time.

The metallic glassy alloy powders for antibacterial coating are mechanically alloyed mixtures of copper, titanium, and nickel nanoparticles. The nanoparticles are alloyed by ball-milling to form glassy, metallic powders. The alloy preferably has a copper:titanium:nickel atomic percentage ratio of about 50:20:30, referred to herein as $Cu_{50}Ti_{20}Ni_{30}$. The powdered alloy is applied to a suitable substrate, such as stainless steel medical instruments, by cold spray powder coating. The coated substrate exhibits antibacterial properties compared to an uncoated substrate.

A method for synthesizing metallic alloy glassy powders comprising disposing metal powders in a ball milling container, the ball milling container including a plurality of milling balls and having an inert atmosphere therein; disposing the ball milling container including the metal powders in a ball mill; operating the ball mill for a period of time to achieve high-energy collision of the plurality of balls with the metal powders in the container, the high energy collision producing a glassy metallic alloy powder. For example, the metal powder can comprises a composition of about 50 percent atomic percent of copper, 20 percent atomic percent of titanium and 30 percent atomic percent of nickel; having the formula $Cu_{50}Ti_{20}Ni_{30}$. For example, the ball mill is operated at rotation speed of at least 235 rotations per minute at room temperature. Typically, a ball to metal powder weight ratio in the ball mill container is about 36:1. For example, the ball milling container is a vial formed from an alloy of chromium and stainless steel having an internal diameter of about 13 cm. The plurality of milling balls can include chromium steel alloy balls having a plurality of first balls having a first size and a plurality of balls having a second size, the first size being different from the second size. The first sized balls can be about 16 mm in diameter and the second sized balls can be about 12 mm in diameter. Generally, the glassy metallic powders have a spherical morphology having a particle size in the range of 0.5 to 3 microns. The inert atmosphere is provided by helium or argon gas.

The method for coating a substrate with metallic glassy powder comprises providing a dry substrate having a surface to be coated; charging the metallic glassy powders obtained from the process of claim 1 in a cold spray feeder; spraying the metallic glassy powders on to the surface in a supersonic jet of inert gas at a flow velocity of at least 1200 m/s thereby coating the surface of the substrate with said metallic glassy powder; and wherein the coating has a uniform thickness. The step of spraying can be repeated at least five times. The step of spraying occurs at a temperature of 400° C. and the substrate can be a sheet of stainless steel. The thickness of the coating can be at least about 10 microns. Preferably, the inert atmosphere is provided by helium or argon gas. Typically, the substrate is pre-cleaned by alumina blasting at room temperature. For example, the substrate coated with metallic glassy powders obtained by the method according to the present method possesses antimicrobial properties. Also, the substrate coated with metallic glassy powders possesses a hardness of 3.1 Gpa.

Ball milling, as used herein, refers to rotation of a hollow cylindrical shell or vial, partially filled with balls to mill or grind a powder mixture disposed in the shell. The shell can be rotated using an attritor, planetary mill or a horizontal ball mill. Ball-milling works on the principle of impact and attrition. Size reduction of the powder is achieved by impact as the balls impact the powder mixture during rotation. Thus, the grinding media is the balls, which may be made of steel such as chrome steel. High energy ball milling is a ball milling process where a powder mixture placed in the ball mill is subjected to high-energy collision with the balls using an attritor, planetary mill or a horizontal ball mill during rotation of the vial containing the balls.

The following examples will further illustrate the ball milling processes of making the metallic glassy alloy powders and the coated metallic alloy composite by cold spraying process but are not intended to limit its scope. In the examples which follow, commercial grade copper, nickel and titanium powders were used. The graphite powders included graphite with particle size of about 20 microns in diameter and had 99.99 wt. % purity. Commercial zirconium (Ti) powders with 150 μm in diameter and 99.99 wt. % purity, PubChem Substance ID GF34772182, provided by SIGMA Aldrich, USA, nickel (Ni) powders with 20 μm in diameter and 99.97 wt. % purity, PubChem Substance ID 266981, provided by SIGMA Aldrich, USA, and copper (Cu) powders with 10 μm in diameter and 99.9 wt. % purity, PubChem Substance 10 203122, provided by SIGMA Aldrich, USA, were used as the starting alloying elements for synthesizing of the metallic glassy powders with nominal composition of $Cu_{50}Ti_{20}Ni_{30}$. The Hydrogen gas ($H_2$) cylinders (99.9990% purity) were provided by a local gas company in Kuwait. The stainless steel vials were made of Cr-steel alloy with an internal diameter of 13 cm and capacity of 1,100 ml was provided by ZOZ (RM20), Germany. 50 Cr-steel alloy balls were used, having a diameter of 16 mm, with 50 Cr-steel alloy balls having 10 mm diameter. Low energy roller-mill type high-energy ball mill, provided by ZOZ, Germany. Helium gas (He) atmosphere-glove box (UNILAB Pro Glove Box Workstation, was obtained from mBRAUN, Germany. Cold-spray coating system was provided by Startack Co. ltd., Japan. Agate mortar and pestle were used as hand mixing tools.

Example 1

Process of Preparing Metallic Glassy Powders

In this process, pure metallic alloying elements of Cu, Ti and Ni powders were used as starting reactant materials. The powders were balanced to give the average nominal composition of $Cu_{50}Ti_{20}Ni_{30}$ and mixed, using an agate mortar and pestle in the glove box filled with a helium gas atmosphere. A certain amount of 100 g of the powders were then charged into a Cr-steel vial (~1,100 ml in volume) and sealed together with 100 balls made of Cr-steel alloy in the glove box. The ball-to-powder weight ratio was selected to be 36:1. The system was then evacuated to the level of $10^{-3}$ bar before introducing purified helium (He) gas atmosphere.

The mechanical alloying process was started by mounting the vial on a roller mill operated at room temperature with a rotation speed of 235 rpm. The progress of solid-state reaction was monitored by interrupting the MA process after selected ball milling time (12.5, 25, 50, 75, and 100 h), where the vial was opened in the glove box to take a represented sample. All samples were characterized by different analytical techniques as discussed below.

Example 2

Metallic Glassy $Cu_{50}Ti_{20}Ni_{30}$ Coated/SUS304 Composite by Cold Spraying Process The fabricated metallic glassy powders obtained alter mechanical alloying for 200 h from Example 1 were used as feedstock materials to coat a sheet strip (~200 mm×40 mm) of SUS304, using a cold spray equipment. The stainless steel sheet, which was firstly rinsed with acetone and ethanol, dried in an oven at 150° C. for 1 h. The surface of the SUS304 substrate sheets was treated by alumina blasting at room temperature. The cold spraying approach was started at low temperature (400° C.) with a supersonic jet processed at a very high velocity (1200 m/s). The powders were charged in cold spray feeder and subjected to high pressure of argon gas flow to pass through pipeline connected to a supersonic jet and then sprayed onto the surface of stainless steel substrate. This process was repeated S times. on each face of the sheet. The as-coated SUS304 sheet had uniform thickness on both faces (upper and bottom faces) of about 10 mm.

The metallic glassy powders were characterized as follows. The average crystal structure of the all powder samples was investigated by X-ray diffraction (XRD) with CuKa radiation, using 9 kW Intelligent X-ray diffraction system, provided by Smartlab-Rigaku, Japan.

The average crystal structure of the all powder samples was investigated by X-ray diffraction (XRD) with CuKα radiation, using 9 kW Intelligent X-ray diffraction system, provided by Smartlab-Rigaku, Japan. The local structure of the synthesized material powders at the nanoscale was studied by 200 kV-field emission high resolution transmission electron microscopy/scanning transmission electron microscopy (HRTEM/STEM) supplied by JEOL-2100F, Japan, equipped with Energy-dispersive X-ray spectroscopy (EDS) supplied by Oxford Instruments, UK. The morphological properties of the powders after selected MA times were determined by 15 kV-field emission scanning electron microscope (FE-SEM, JSM-7800F, Japan) equipped with EDS supplied by Oxford Instruments, UK.

The concentrations of elemental Cu, Ti, and Ni in the as-ball milled powders were determined by different techniques, such as inductively coupled plasma optical (ICP) emission spectrometry, TEM/EDS and SEM/EDS. The oxygen contamination content was determined by the helium carrier fusion-thermal conductivity method. The powders of the end product (200 h) were slightly contaminated with Fe (0.21 atomic %), Cr (0.08 atomic %) and oxygen (0.22 atomic %).

A Shimadzu Thermal Analysis System/TA-60WS, using differential scanning calorimeter (DSC) was employed to investigate the thermal stability of the as-ball milled powders, indexed by the transition glass crystallization ($T_x$), and enthalpy change of crystallization ($\Delta H_x$), using a heating rate of 40° C./min.

The crystal structure of the as-cold-sprayed $Cu_{50}Ti_{20}Ni_{30}$ coated/SUS304 was characterized by XRD and compared with the as-prepared metallic glassy powders. Intensive surface morphological characterizations and local compositions of the coated samples were achieved by SEM/EDS technique. The tribological behavior of the metallic glassy coatings was characterized by a pin-on disc tribometer (MICROTEST, S.A, Madrid-Spain) against a hard ball (10 mm in diameter) made of WC—Ni composite. The sliding speed of the specimen relative to the ball was $5 \times 10^{-2}$ m/s, the sliding distance was 100m with a total sliding time of 950 s, and the normal load applied load was 10N. The coefficient of friction (CPF) of the sliding couple was continuously recorded during the test. The surface of the samples was examined after the wear test, using SEM/EDS approach.

Bacterial strains as test organisms used for the trials were *Escherichia coli* (ATCC 25922). Biofilms were grown according to Al-Azemi et al. 2011, with the following modifications; planktonic cells were grown in brain heart infusion (BHI) (Oxoid, UK). Biofilms were grown on 22-mm$^2$ coated coupons. Sterile coupons were positioned vertically in 50-ml conical tubes (BD) Falcon, Franklin Lakes, N.J.) with 6 ml pre-warmed BHI.

The tested coupons were inoculated with 100 μl 0.5 McFarland standard suspensions (equivalent to $1.5 \times 10^8$ CFU ml$^{-1}$) of a 24 h culture. Biofilms were left to grow for various period of time (24, 48 and 72 h) at 37° C.

The effect of metallic glassy coating on biofilm formation was investigated. Assays were modified from the method described by McAuliffe et al. 2006, and Al-Azemi et al. 2011. Briefly, 24, 48 and 72 hours-old biofilm were used as previously described. Triplicate coupon were taken to prepare biofilms, 22 mm$^2$ $Cu_{50}Ti_{20}Ni_{30}$ coating/SUS304 coupons were rinsed in PBS to remove nonadherent cells and placed in BHI (7 ml). Tested coupon were vortexed for 15 min to remove the biofilm cells. Viable bacteria were then enumerated.

The XRD patterns of mechanically alloyed $Cu_{50}Ti_{20}Ni_{30}$ powders obtained after different stages of ball milling time are shown in FIG. 1. The starting reactant powders (0 h) had large polycrystalline grains of the alloying elements, indicated by the sharp Bragg peaks of fcc-Cu (PDF#00-004-0836), hcp-Ti (PDF#00-005-0682), and fcc-Ni (PDF#00-004-0850), as shown in FIG. 1A.

Figure 2A:
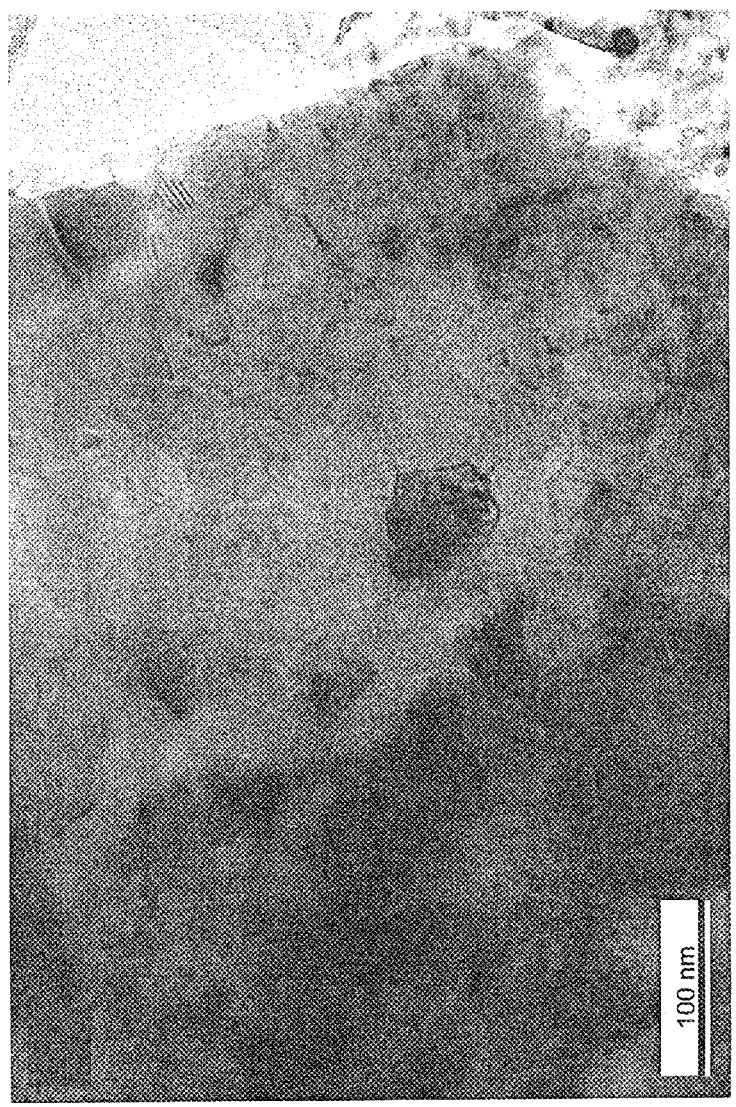
FIGS. 2A, 2B, and 2C are scanning electron micrographs (SEMs) showing the BFI, DFI, and SADP, respectively, of mechanically alloyed $Cu_{50}Ti_{20}Ni_{30}$ powders obtained after 12 h of the ball milling time.
Figure 2B:
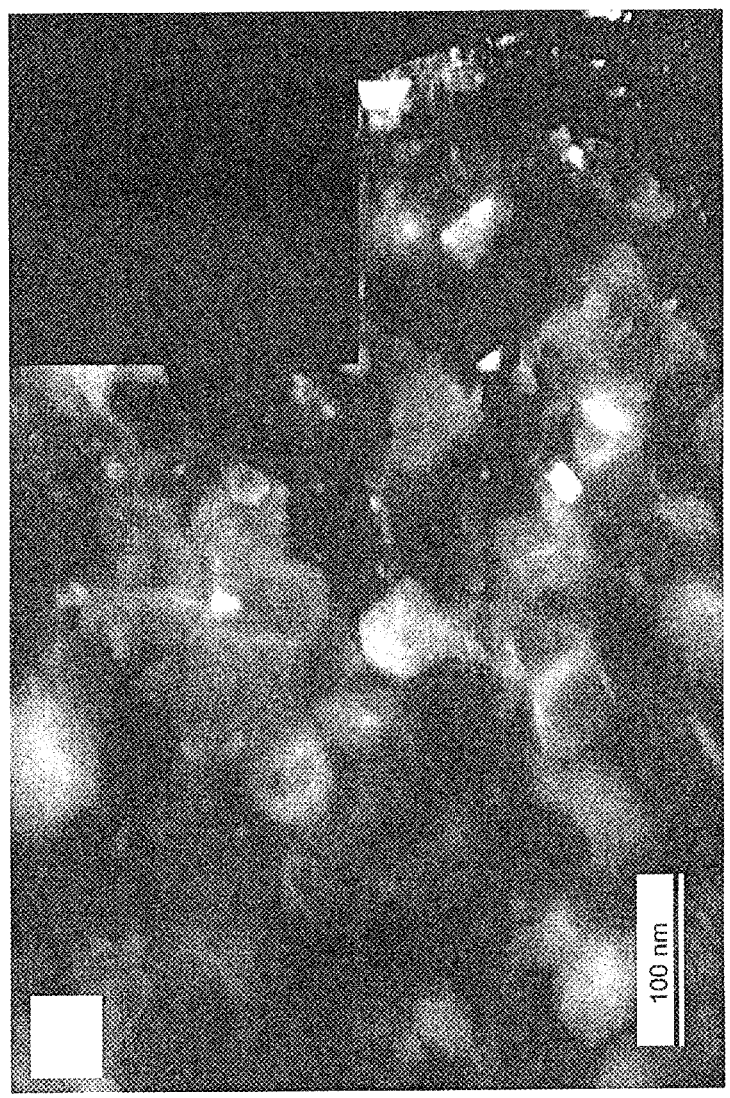
Figure 2C:
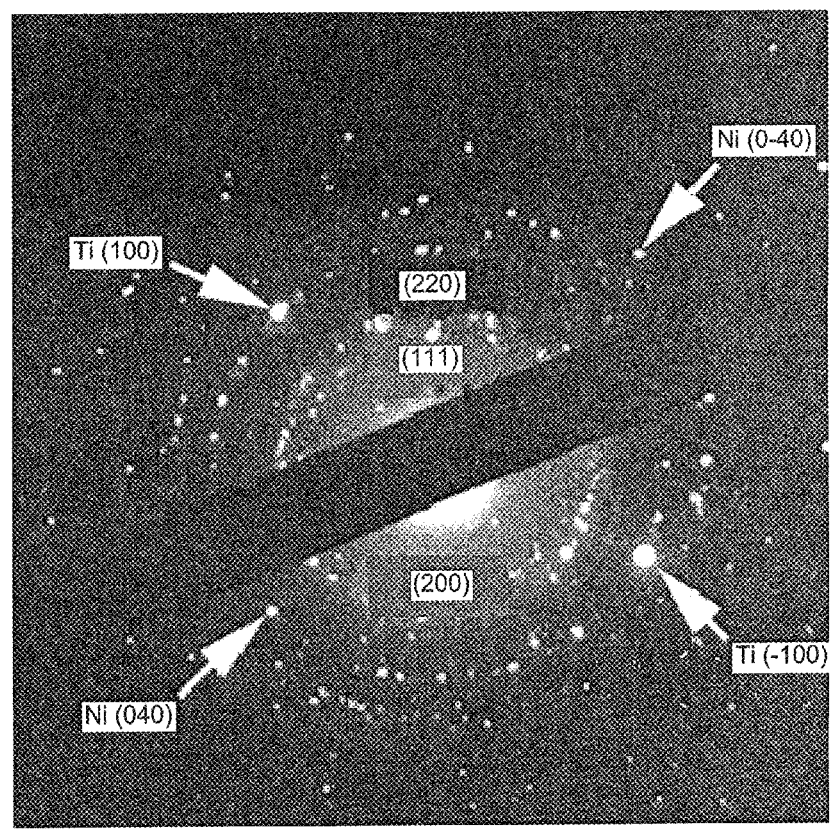

The bright field image (BFI) and the dark field image of the powders obtained after 12 h of the mechanical alloying (MA) time are shown in FIGS. 2(A) and 2(B), respectively. After this early stage of MA time, the powders were suffered from severe mechanical deformation led to lattice imperfections, as suggested by the nano twins, dislocations and point defects appeared in the grains of the alloying elements, as displayed in FIG. 2A. The grain sizes of the powders had a large size distribution, ranging from 10 nm up to 73 nm in diameter (FIG. 2B). The crystal structure of the powders after this stage of ball milling was a polycrystalline mixture of the three alloying elemental phases with the absence of any amorphous and/or reacted metastable phase. This was confirmed from the spots and Dybe-Scherrcr's rings shown in the selected area diffraction pattern (SADP) in FIG. 2C.

Figure 1B:
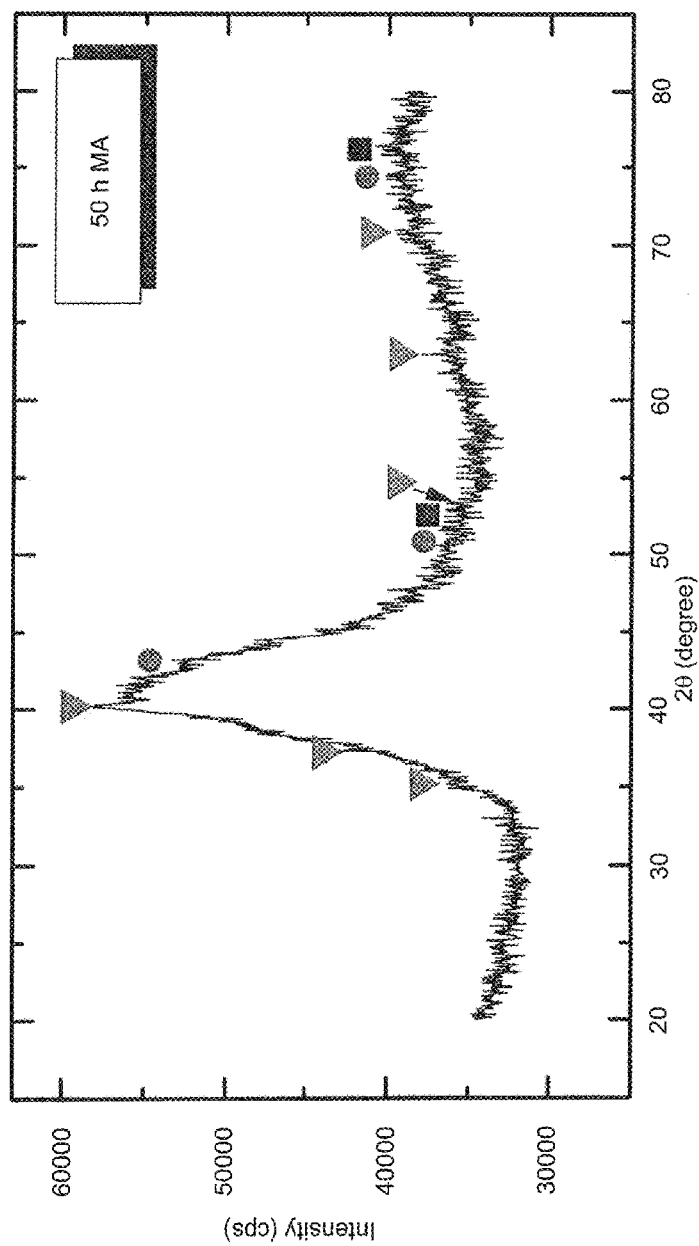

Further MA time (50 h) led to enhance the mechanically-induced solid-state reactions of the alloying elements, indicated by disappearance of the minor Bragg peaks related to the pure elemental powders, as shown in FIG. 1B. Moreover, significant decreasing in the intensities related to major Bragg peaks of Cu(111), Ti(001) and Ni(111) were achieved. In addition, clear first (~35° to 480) and second (~64° to 80°) broad diffuse haloes appeared, implying the formation of an amorphous phase coexisted with unprocessed nanocrystalline Cu and Ti powders, as elucidated in FIG. 1B.

Figure 3A:
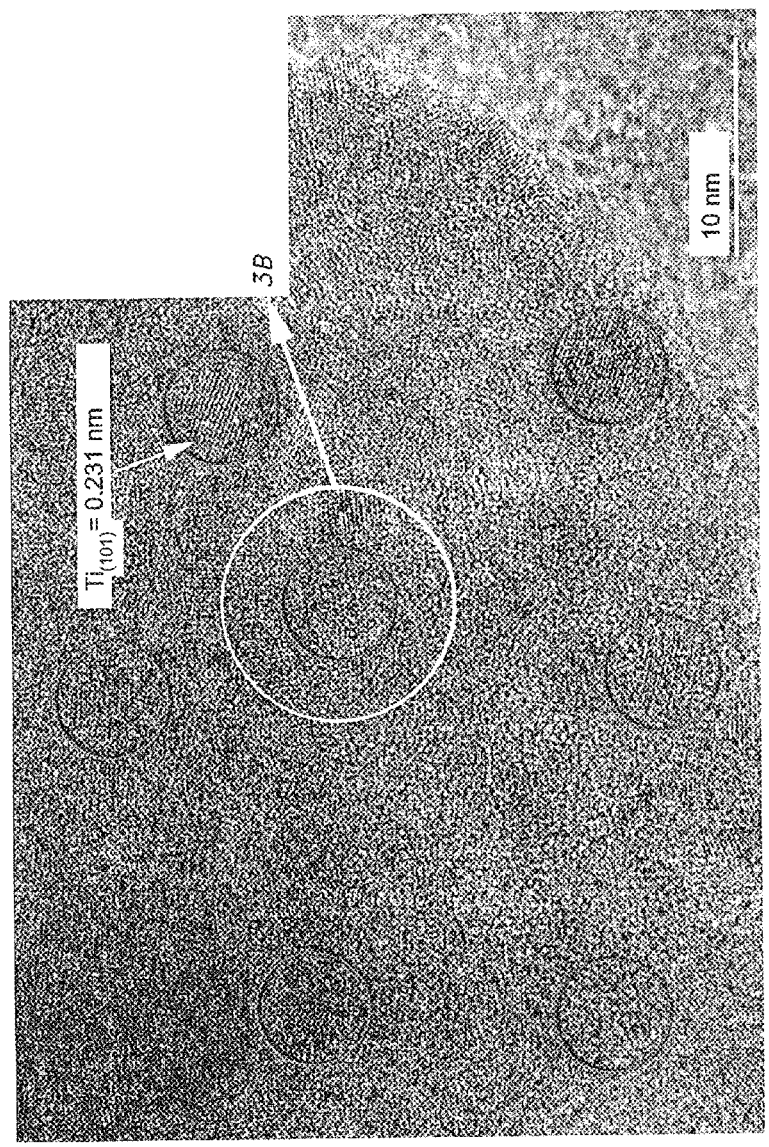
FIG. 3A is the high resolution transmission electron micrograph (HRTEM) image and of the powders obtained after 75 h of the ball-milling time.

Increasing the MA time to 75 h led to increase the volume fraction of the amorphous phase against the unprocessed crystalline powders, as shown in FIG. 3A. However, careful local examination of the sample obtained after 75 h of MA time, indicated the precipitation of nanocrystalline cells (less than 5 nm in diameter) of Cu, Ti and Ni powders into the maze-like structure of the amorphous matrix, shown in FIG. 3A.

Figure 3B:
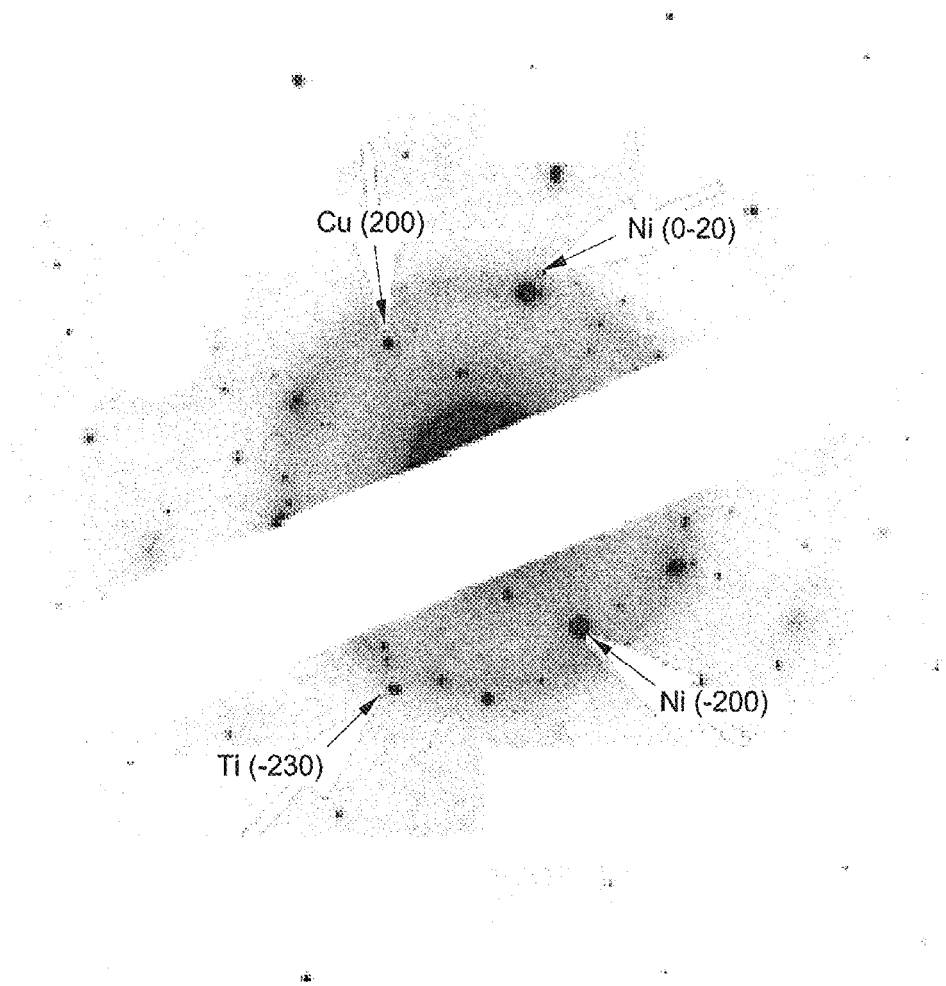
FIG. 3B is the corresponding Nano Beam Diffraction Pattern (NBDP).

The existence of these clusters were confirmed by the nanobeam diffraction pattern (NBDP), which was taken from the large white circle (~10 nm), revealing halo diffraction rings overlapped with crystalline sports related to Cu, Ti and Ni crystals (FIG. 3B).

In order to investigate the local composition of the powders obtained after this intermediate stage of ball milling (75 h), EDS analysis with a beam spot of about 5 nm in diameter was performed at the 6 zones indexed by the small blue circles shown in FIG. 3A. The ED5 compositional analysis (in atomic percent) for the selected zones is listed in Table 1. Remarkable fluctuations in the powder composition beyond the atomic scale can be hardly seen, suggesting the formation of rather homogeneous amorphous phase. Table 1 displays the local EDS elemental analysis of the points presented in FIGS. 3A-3D respectively.

TABLE 1

Elastic Recoil Detection (ERD) compositional analysis

| Points | Cu | Ti | Ni | Total |
|---|---|---|---|---|
| Mechanically Alloyed $Cu_{50}Ti_{20}Ni_{30}$ Powders for 75 h | | | | |
| 1 | 50.07 | 19.83 | 30.10 | 100 |
| 2 | 49.89 | 19.95 | 30.16 | 100 |
| 3 | 50.05 | 19.74 | 30.21 | 100 |
| 4 | 49.86 | 20.16 | 29.98 | 100 |
| 5 | 50.18 | 19.91 | 29.91 | 100 |
| 6 | 49.99 | 19.95 | 30.06 | 100 |
| 7 | 50.09 | 20.07 | 29.84 | 100 |
| Average | 50.02 | 19.98 | 30.03 | 100 |
| Mechanically Alloyed $Cu_{50}Ti_{20}Ni_{30}$ Powders for 100 h | | | | |
| 1 | 50.07 | 20.04 | 29.89 | 100 |
| 2 | 49.97 | 19.96 | 30.07 | 100 |
| 3 | 50.04 | 19.93 | 30.03 | 100 |
| Average | 50.03 | 19.98 | 29.99 | 100 |

Figure 1C:
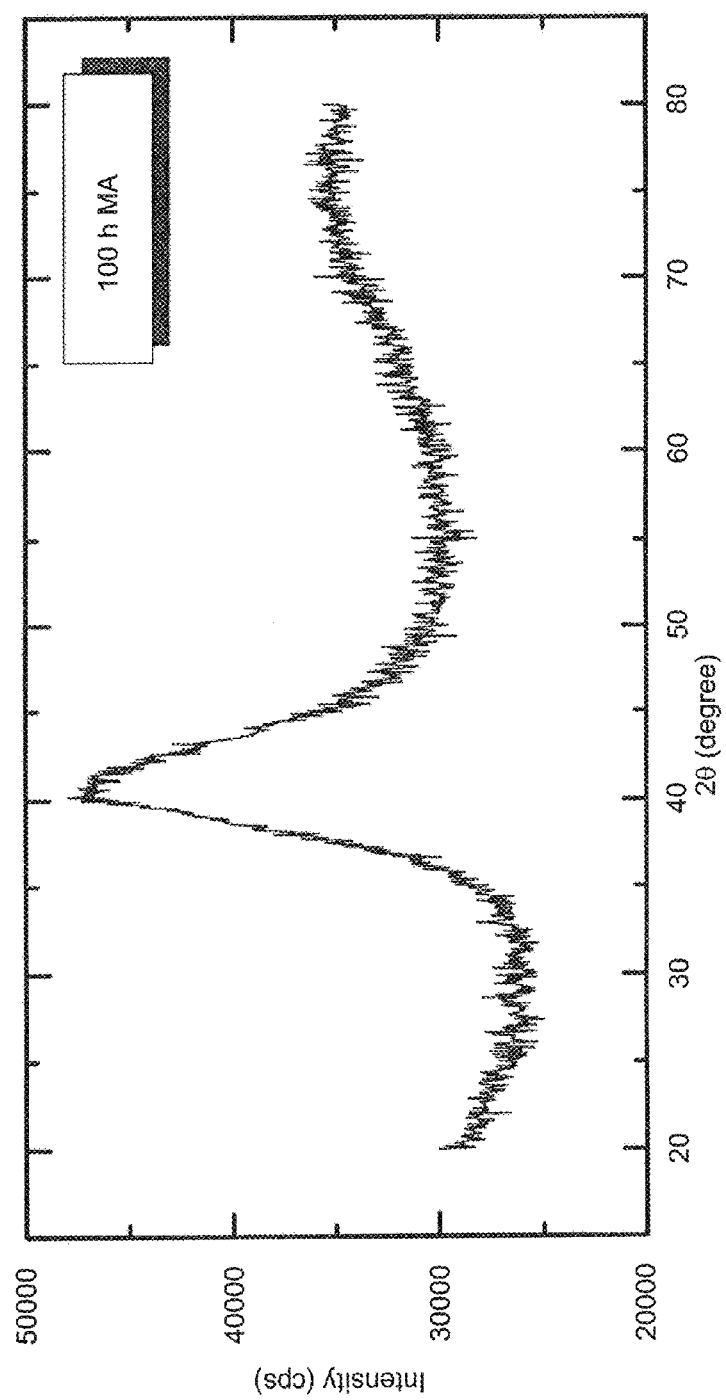

The XRD pattern of the powders obtained after the end-stage of ball milling (100 h MA) revealed a homogeneous diffuse halos, as shown in FIG. 1C. Moreover, those Bragg peaks related to the starting alloying elements disappeared, suggesting the completion of the mechanically-induced solid-state reaction and the formation of a single amorphous phase.

Figure 3C:
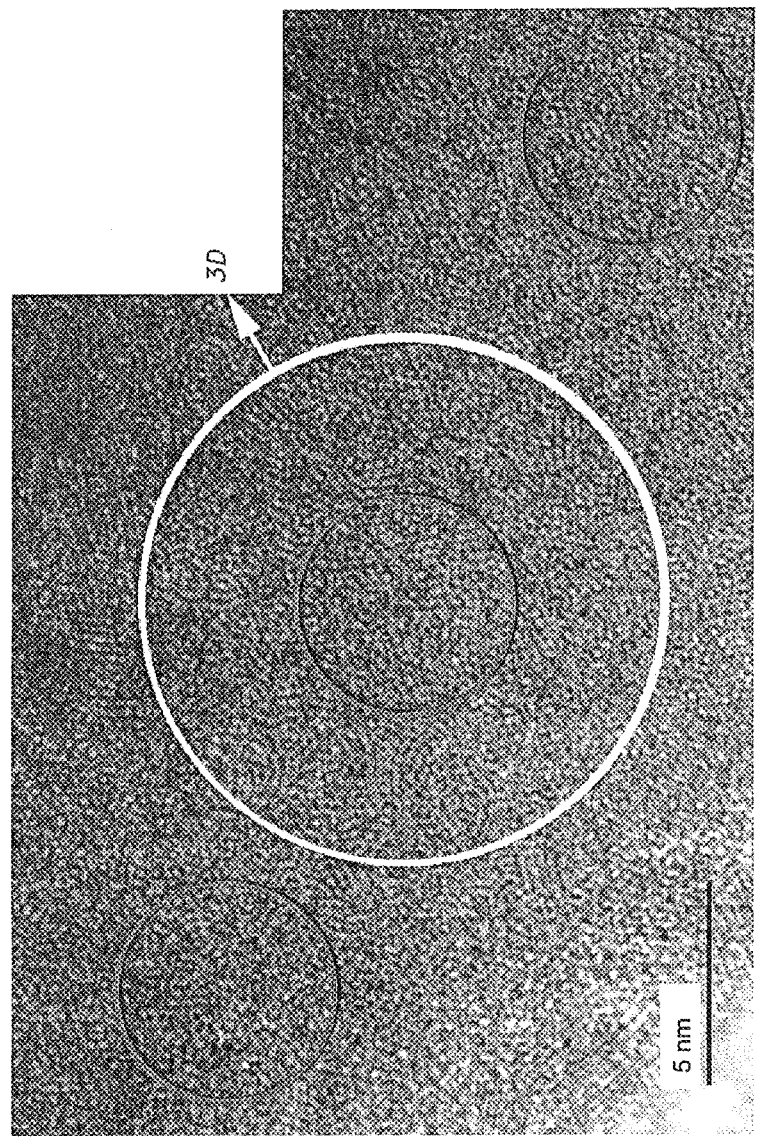
FIG. 3C is the high resolution transmission electron micrograph (HRTEM) image of the powders for end-product (100 h)
Figure 3D:
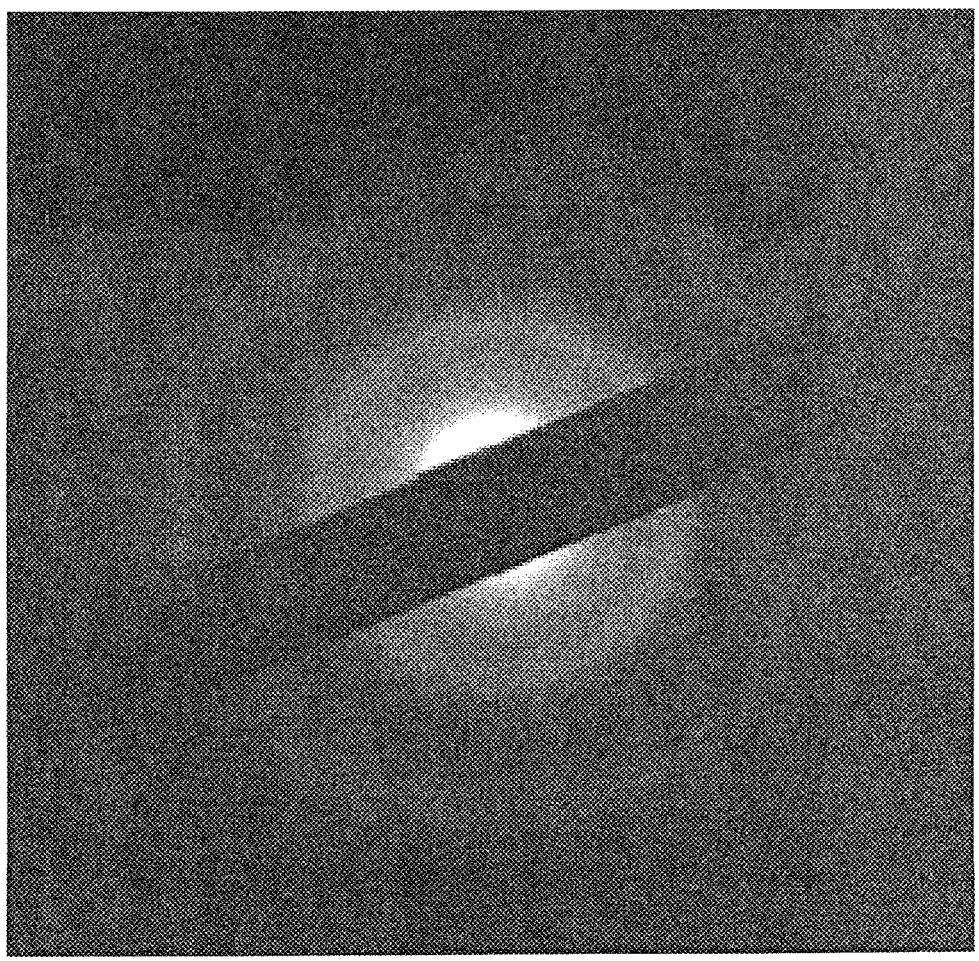
FIG. 3D is the corresponding Nano Beam Diffraction Pattern (NBDP).

The high resolution transmission electron micrograph HRTEM image and corresponding NBDP of the powders obtained after 100 h of MA time are shown in FIGS. 3C and 3D, respectively. Overall, the sample appeared featureless and homogeneous in its internal structure with no indication of precipitations of any crystalline phases, as shown in FIG. 3C. In addition, the powders revealed maze contrast of a dense-packed metallic amorphous, suggesting the formation of homogeneous amorphous phase within the nanoscale. Moreover, the NBDP (FIG. 3D taken from the middle part of the sample (white circle in FIG. 3C) displayed a typical halo-diffraction of an amorphous phase with the absence of sharp rings and/or spots related to the unprocessed crystalline powders. In contrast to the powders obtained after 75 h of MA time, the local EDS analysis of 3 selected zones (Table 1) indexed by the blue circles showed very closed values, implying the formation of a homogeneous $Cu_{50}Ti_{20}Ni_{30}$ powders.

Figure 4A:
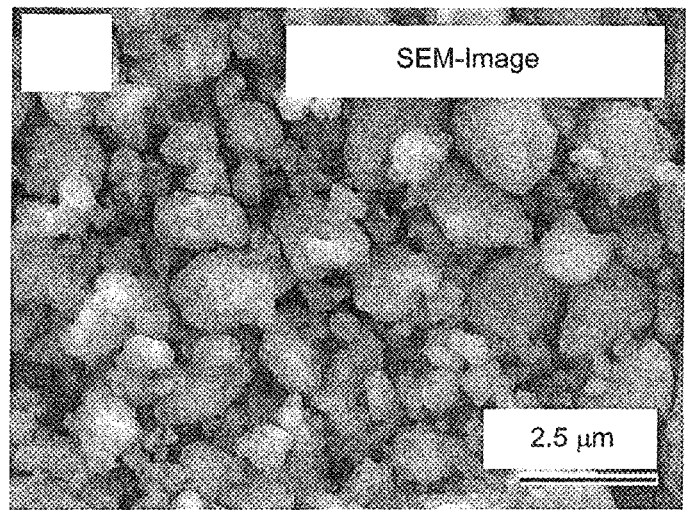
FIG. 4A shows the Scanning Electron Micrograph (SEM) micrograph of mechanically alloyed $Cu_{50}Ti_{20}Ni_{30}$ powders obtained after 100 h of the ball-milling time.
Figure 4B:
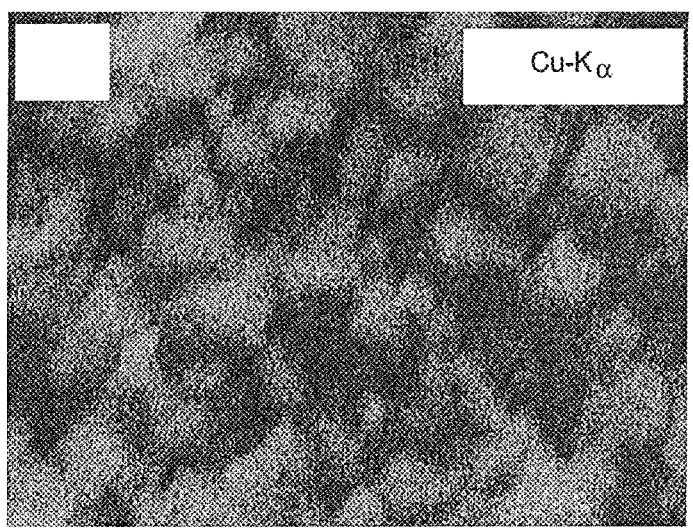
FIGS. 4B, 4C, and 4D are the corresponding X-ray elemental mapping for Cu, Ti, Ni, respectively.
Figure 4C:
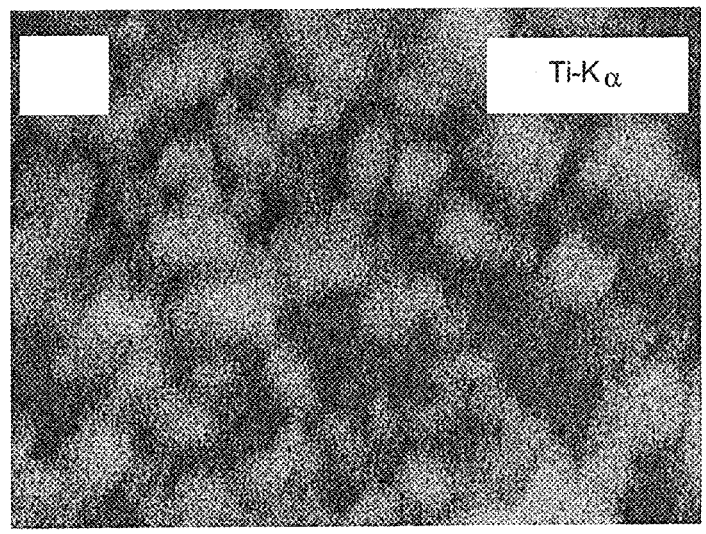
Figure 4D:
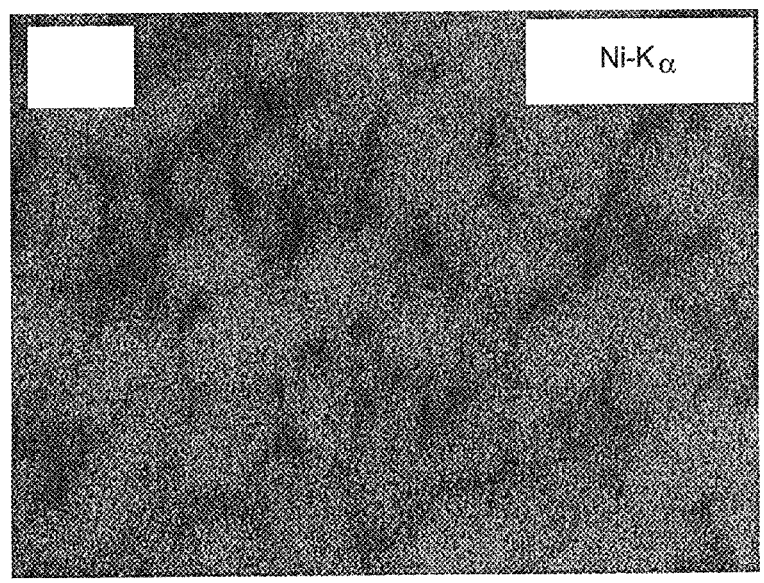

The morphological characterization of $Cu_{50}Ti_{20}Ni_{30}$ amorphous powders obtained after 100 h of MA time was examined by FE-SEM. The apparent particle size of the powders ranged from 0.8 µm to about 2.5 µm in diameter, as shown in FIG. 4A. A single agglomerated particle consisted of ultrafine spherical powders of less than 1 µm in diameter. The composition and elemental distribution of the as-synthesized $Cu_{50}Ti_{20}Ni_{30}$ amorphous powders were further mapped through EDS by displaying the integrated intensity of Cu, Ti and Ni signals, as shown in FIG. 4. The results shown in FIGS. 4B-D reveal that the three alloying elements of were distributed very homogeneously in the micro-scaled powders and exhibited no apparent element separation or aggregation. Moreover, the Cu/Ti/Ni ratio measured from several micro-scaled powders with EDS analysis showed an average atomic % ratio of 50.18/19.91/29.91.

Figure 5A:
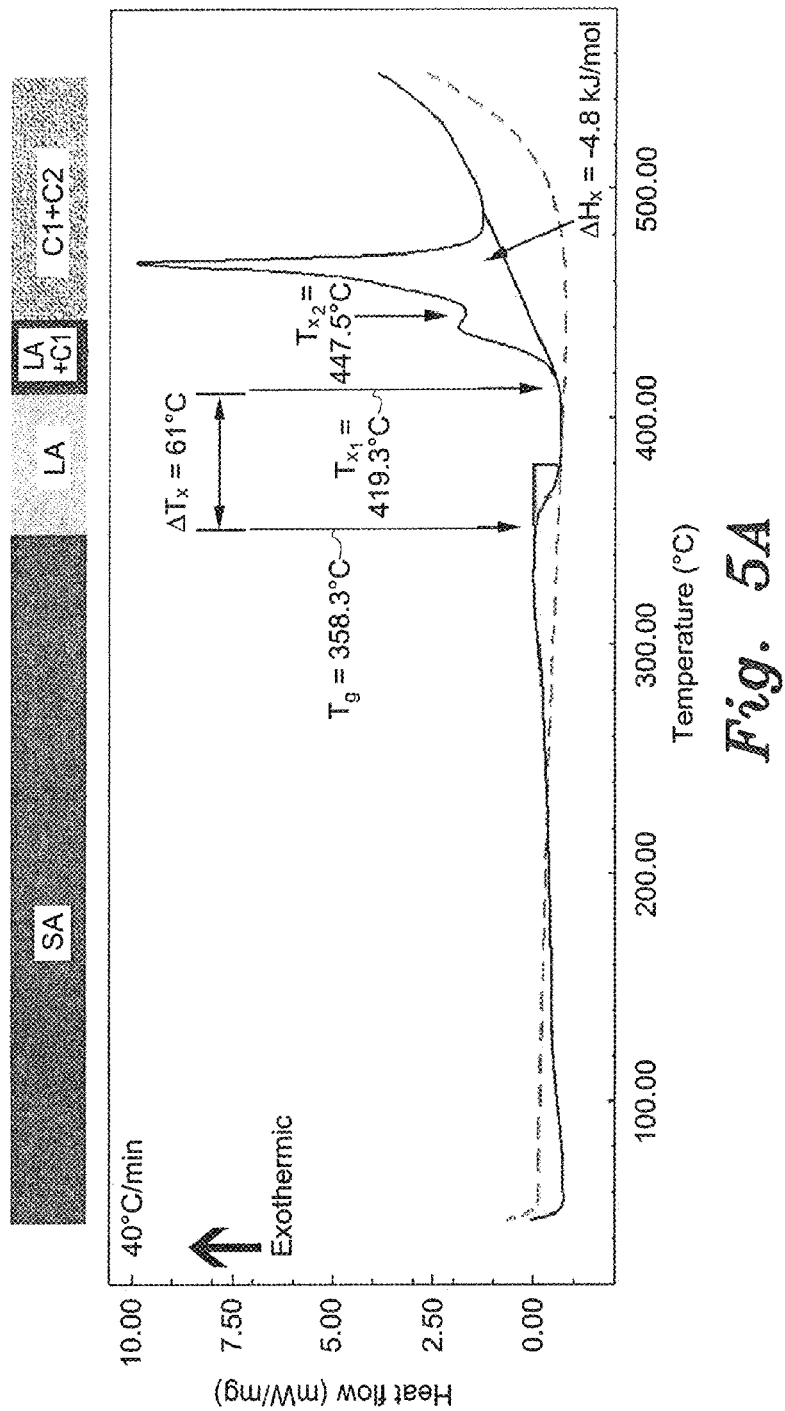
FIG. 5 A is the differential scanning colorimetry (DSC) thermogram of the powders obtained after 100 h of the ball-milling time.
FIGS. 5B, 5C, and 5D are HRTEM micrographs for the samples heated in the DSC up to 400° C., 420° C., and 560° C., respectively.

The DSC scan of $Cu_{50}Ti_{20}Ni_{30}$ powders obtained after 100 h of MA time conducted with a heating rate of 40° C./min is shown in FIG. 5A. The solid line presents the first heating run, whereas the dashed line achieved in the same temperature range of 500° C. to 560° C. under the same heating rate. The scan of the powders revealed three reactions, as displayed in FIG. 5A. The first, which occurred at an onset temperature of 358.3° C. is an endothermic reaction, whereas the second and third ones were exothermic reactions taking place at onset temperatures of 419.3 and 447.5° C., respectively. All of these reactions disappeared during the second heating run, as elucidated in FIG. 5A.

Figure 5B:
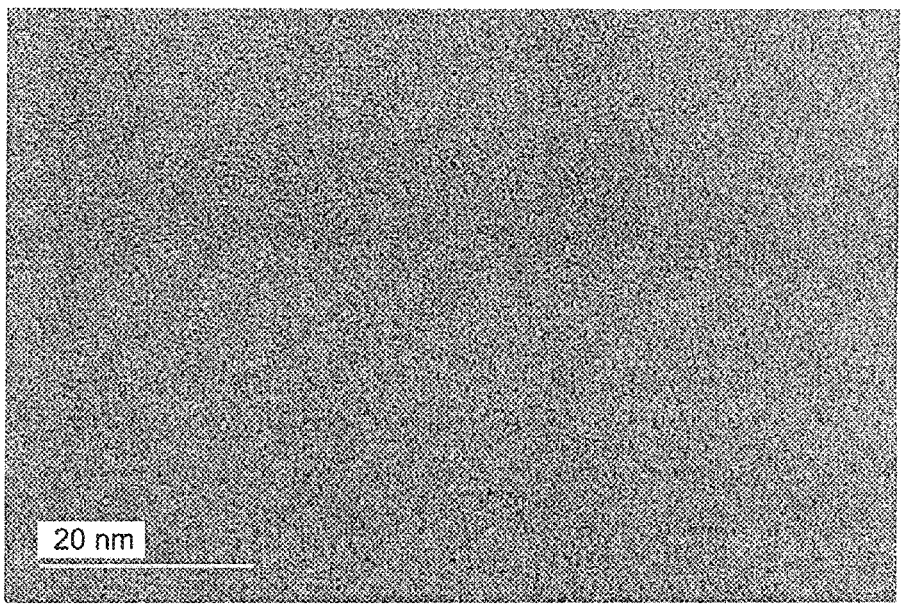

In order to understand the nature of each reaction, a third heating run was perform up to the onset temperature of the endothermic peak (358.3° C.) and then immediately cooled down to the room temperature. A fourth heating run was conducted up to 400° C. In this heating run, which was followed by cooling and then another heating runs, the same endothermic peak was observed. This implies that the endothermic peak shown in FIG. 5A was related to the solid-amorphous (SA) to liquid-amorphous (LA) transformation taking place at a glass transition temperature ($T_g$) of 358.3° C. The HRTEM image of the sample heated up to 400° C. had a maze featureless structure of an amorphous phase without any contrasts of crystalline phase(s), implying the existence of a single metallic glassy $Cu_{50}Ti_{20}Ni_{30}$ phase, as shown in FIG. 5B.

Figure 5C:
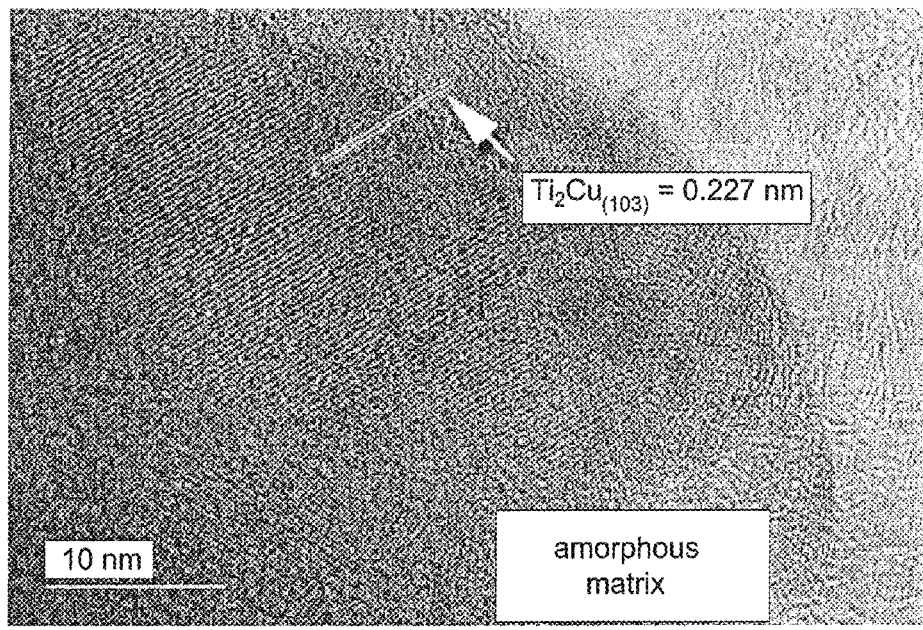

A minor exothermic reaction was developed upon continuous heating of the powders up to 419.3° C. and followed by a sharp pronounced exothermic peak appeared at 447.5° C., as shown in FIG. 5A. The HRTEM image of the sample taken at 420° C. shows the precipitation of primary crystalline phase (C1) embedded into the amorphous matrix, as shown in FIG. 5C. The Moire fringes in FIG. 5C are related to the interplaner spacing of $Ti_2Cu(103)$ (0.2280 nm), as confirmed by the reported data (PDF#00-015-0717). Thus, the first exothermic peak corresponding to the crystallization of TbCu phase at a crystallization temperature ($T_{x1}$) of 419.3° C. The area existed between just above the $T_g$ and below $T_{x1}$ is known as supercooled liquid region ($\Delta T_x$) and refers to the format ion of highly viscus liquid amorphous phase (metallic glassy phase).

Figure 5D:
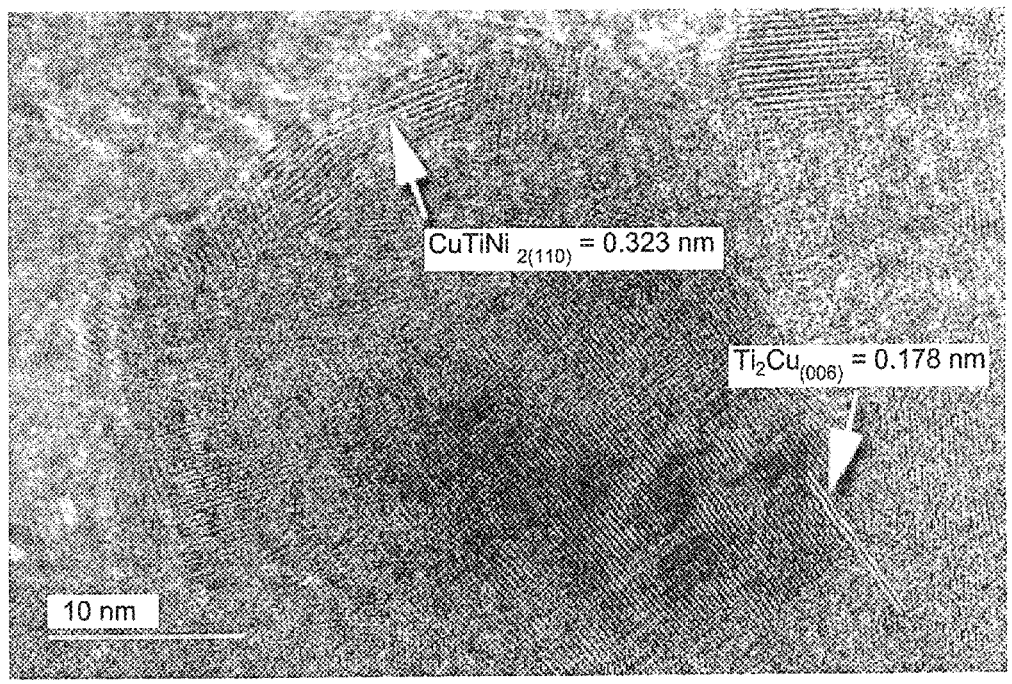

The enthalpy change of crystallization of the first exothermic reaction ($\Delta H_{x1}$) was calculated from the area under the first crystallization peak and found to be −1.13 kJ/mol. The second exothermic peak taking place at 447.5° C. ($T_{x2}$)

is attributed to the crystallization of the residual CuTiNi$_2$ (PDF#04-003-9278) amorphous phase. The HRTEM image of the sample taken after the completion of the second exothermic reaction (~560° C.), shows the formation of nanocrystalline grains of mixed Ti$_2$Cu and CuTiNi$_2$ phases with the absence of the amorphous phases, as confirmed by the lattice-fringe images shown in FIG. 5D. The $\Delta H_{x2}$ of amorphous was calculated from the area under the second crystallization peak and found to be −3.67 kJ/mol.

Based on the results derived from the DSC experiments, we can conclude that SA Cu$_{50}$Ti$_{20}$Ni$_{30}$ powders transforms into a LA-phase upon heating up to 358.3° C. This metallic glassy phase maintained its short-range ordered structure in a wide temperature range reached to 61° C. However, it tended to crystallize through two crystallization steps to form nanocrystalline grains of Ti$_2$Cu and CuTiNi$_2$ phases at temperatures of 419.3° C. and 447.5° C., respectively with a total $\Delta H_x$ of −4.8 kJ/mol.

Figure 6:
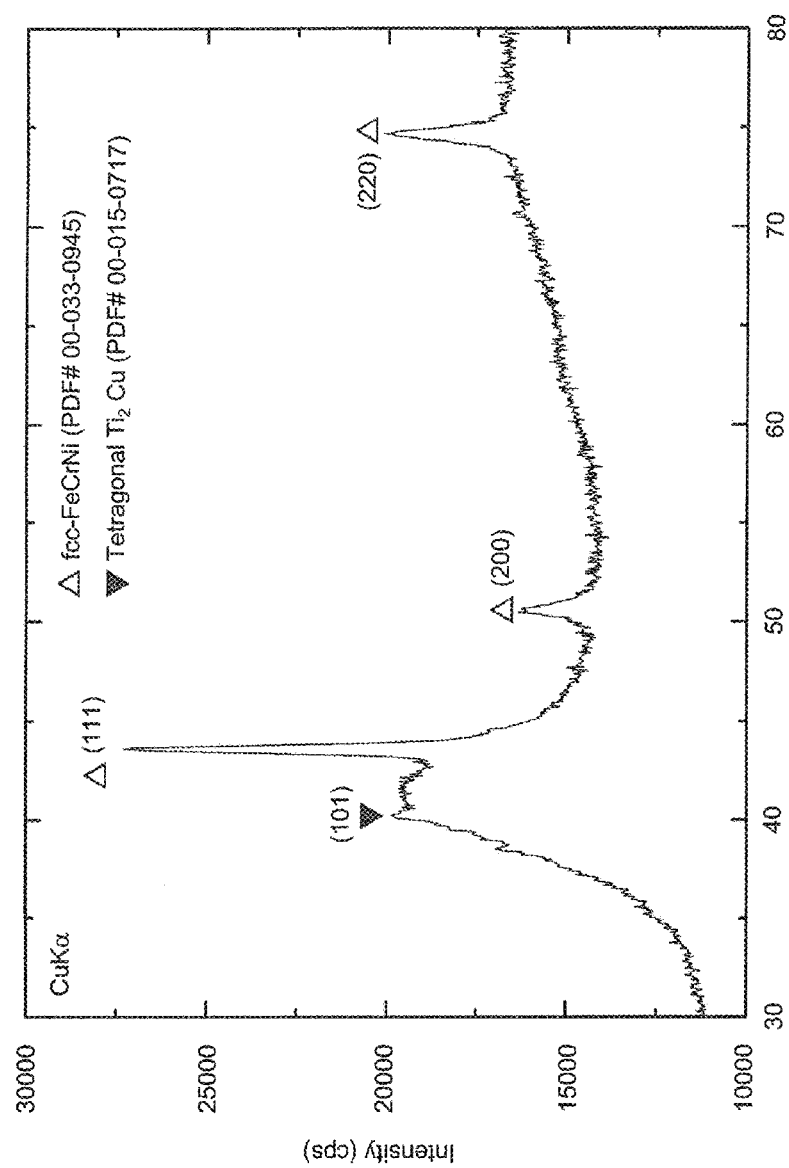
FIG. 6 is the XRD spectrum of cold spray metallic glassy $Cu_{50}Ti_{20}Ni_{30}$ powders coated on an SUS304 surface.

The as-synthesized metallic glassy powders obtained after 100 h of MA time were employed in the present disclosure as antibacterial feedstock materials for coating stainless steel sheet (SUS304), using cold spraying technique. According to the target of the present work, the applied temperature of the cold spraying process was 400° C. (just above the Tg of the glassy powders (FIG. 5A). The XRD pattern of as-cold sprayed Cu$_{50}$Ti$_{20}$Ni$_{30}$ coating is shown in FIG. 6. The coating deposit revealed a broad halo-diffuse pattern, indicating a successful cold spraying procedure for maintaining the amorphous structure of the glassy powders during the spraying process. However, a weak crystalline Bragg peak related to crystalline Ti$_2$Cu phase is existed with the first halo (~39°), suggesting a minor crystallization and the formation of a small volume fraction of Ti$_2$Cu nanocrystalline phase. The formation of this phase was probably developed during the rather long period of time (40 min) needed to cool the as-coated system before handling. Since the thickness of the coating obtained in the present study was about 1.4 µm, the Bragg peaks of the substrate materials (austenitic SUS304) were diffracted and sharply appeared in the XRD pattern shown in FIG. 6.

The cold spray Cu$_{50}$Ti$_{20}$Ni$_{30}$ coated SUS304 composite layer coated material consisted of a substrate Fe-18Cr-8Ni (SUS 304) substrate coated by a thin layer of metallic glassy powders. The coating materials were uniformly distributed on the surface of the substrate with the absence of uncoated zones as indicated by the near thickness values of the coated layer. The EDS analysis of the coated zone containing about 35 individual test points were translated into isochemical contour maps of Cu, Ti and Ni. The EDS results revealed homogeneous elemental distributions within the microscale with the absence of obvious compositional fluctuations or degradations.

Based on the local compositional investigations performed by EDS analysis, one can say that cold spraying approach did not lead to compositional changes during processing and the alloying elements of the metallic glassy phase presented by their three alloying elements were homogeneously distributed without apparent element separation or aggregation. Moreover, the Cu/Ti/Ni ratio measured from several points with EDS analysis showed an average at % ratio of 49.83/20.07/30.10, which is being very close to the nominal average composition of the starting Cu50Ti20Ni30 powders.

The success of obtaining a dense glassy coating materials with amorphous random structure is challengeable and can be achieved with those metallic glassy system showing large $\Delta T_x$ region (above 40° C.). It is realized that metallic glassy alloys show superplasticity in the supercooled liquid state due to Newtonian viscous flow. Thus, cold spraying at a temperature laid in such a viscous region when the amorphous Cu$_{50}$Ti$_{20}$Ni$_{30}$ alloy powders alloys shows viscous flow led to support bonding to the SUS304 substrate.

Figure 7A:
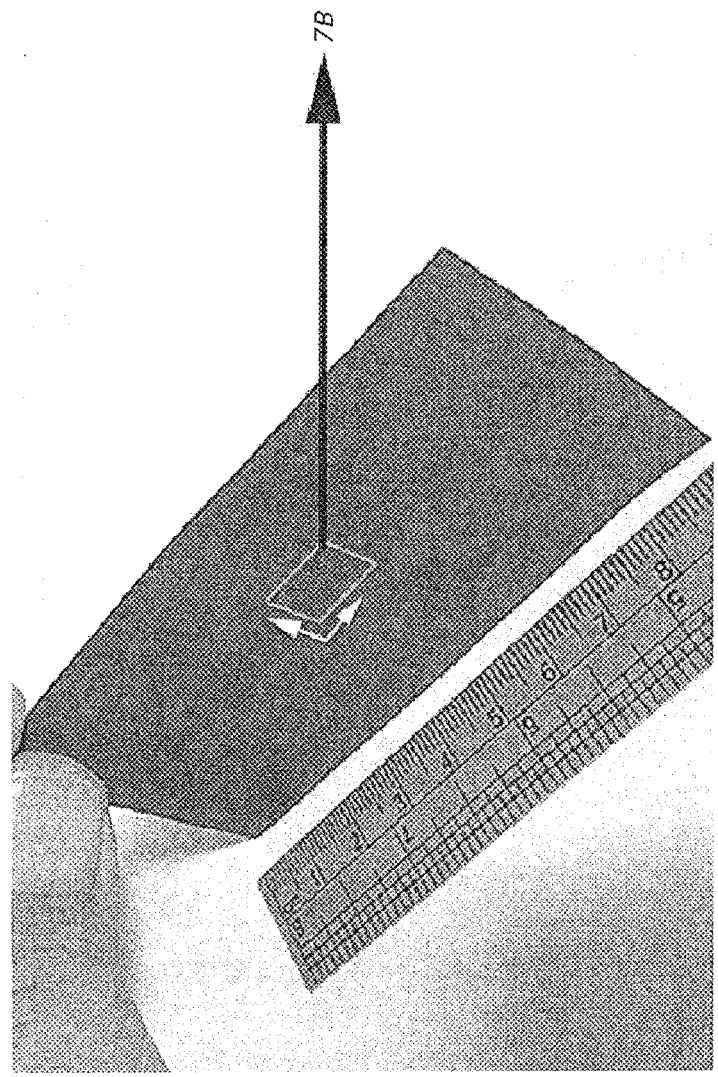
FIG. 7A is a photograph of the strip portion (~9 cm×5 cm) of a cold spray metallic glassy $Cu_{50}Ti_{20}Ni_{30}$ powders coated SUS304 substrate.

Nanomechanical properties of metallic glassy Cu$_{50}$Ti$_{20}$Ni$_{30}$ coated SUS304 indexed by nanohardness and Young's modulus was performed, using nanoindentation test. A small portion (1.5 cm×1.0 cm) of the as-coated SUS304 strip (the squared region shown in FIG. 7A was classified into 70 sub-zones FIG. 7B where the nanoindentation examinations were achieved with a load of 400 mN at the red circular points elucidated in FIG. 7B. The nanohardness and Young's modulus obtained upon testing 88 points were plotted accordingly in FIGS. 7C and 7D respectively. Metallic glassy Cu$_{50}$Ti$_{20}$Ni$_{30}$ coating material possessed extraordinary high microhardness values, ranging between 2.97 GPa to 3.20 GPa, as presented in FIG. 7C. Moreover, the value of the Young's modulus measured at the 88 selected points showed a variation in the between 97 GPa to 111 GPa depending on the XY coordination of each examined point. The closed nanohardness and Young's modulus values and the absence of random results suggesting the uniformity and homogeneity in structure and elemental composition of the cold-sprayed metallic glassy coated SUS304 material.

Figure 8:
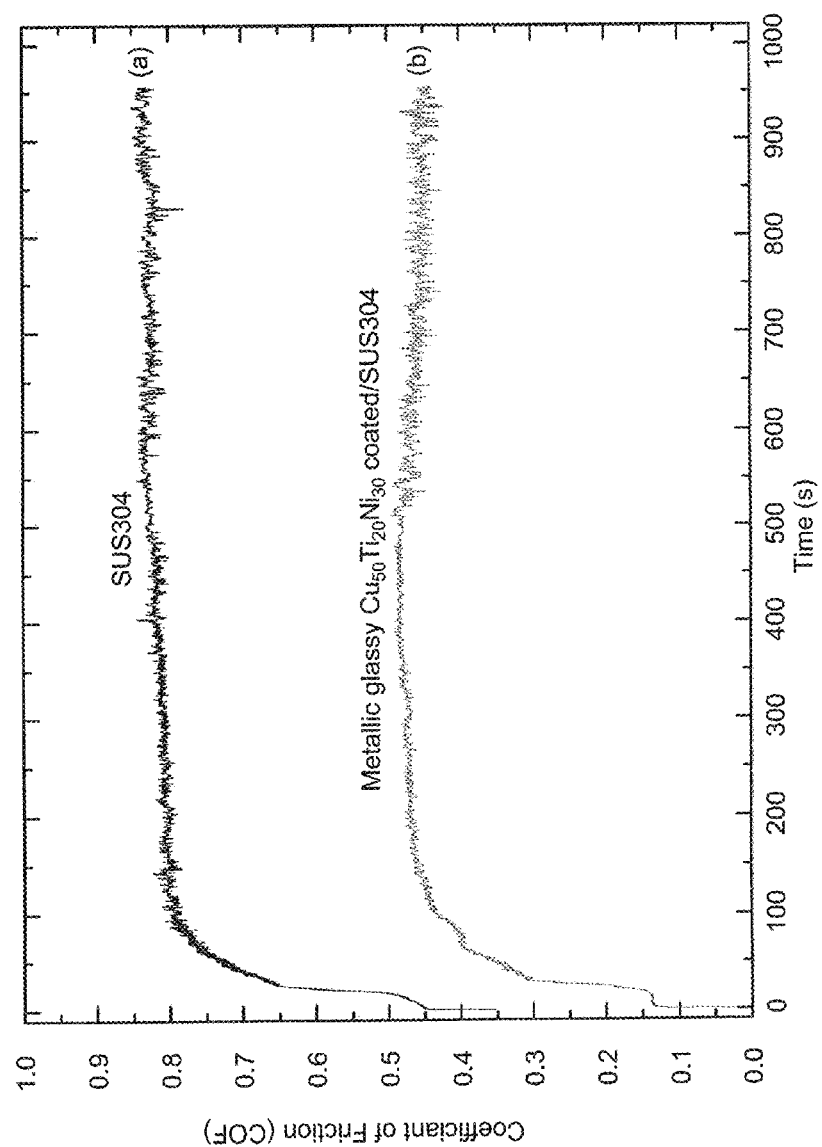
FIG. 8 is a graph depicting the dynamic coefficient of friction as a function of time for an uncoated SUS304 substrate (curve (a)) and a cold spray metallic glassy $Cu_{50}Ti_{20}Ni_{30}$ powders coated SUS304 substrate (curve (b)).
Figure 9A:
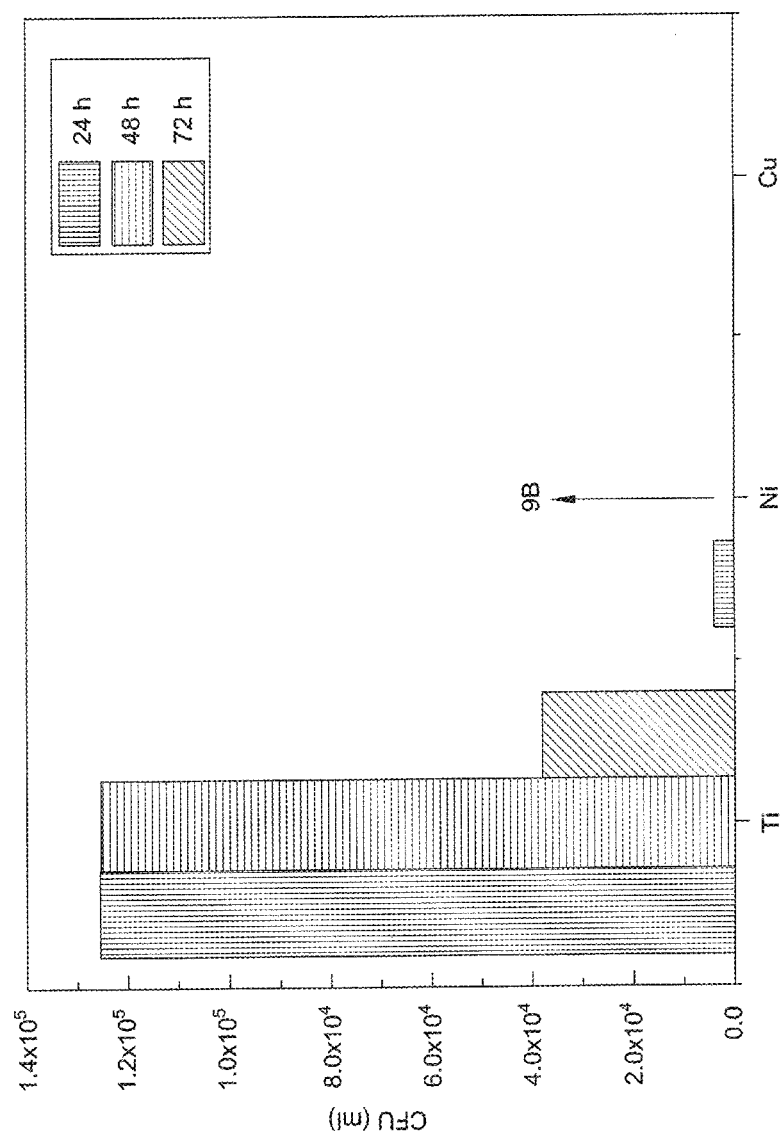
FIG. 9A is a chart showing biofilm formation by *E. coli* on a TM-coated SUS 304 substrate.
Figure 9B:
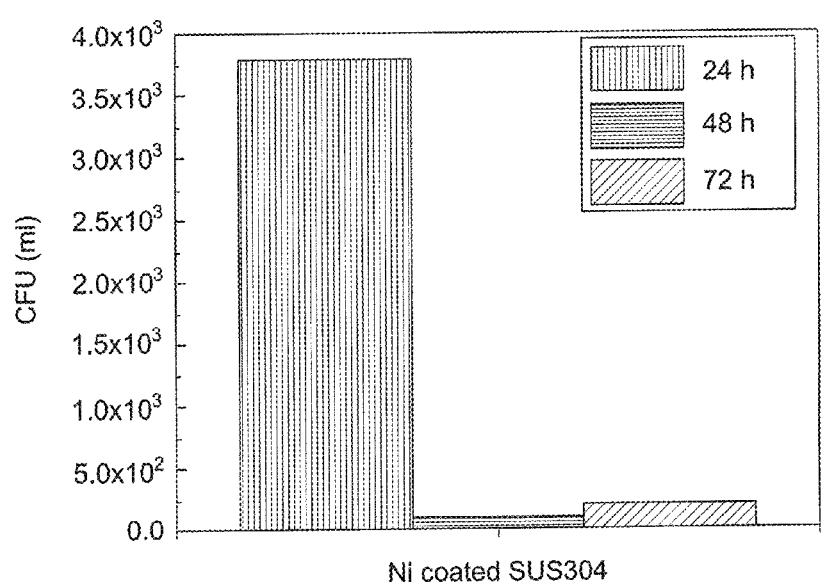
FIG. 9B is a chart showing biofilm formation by *E. coli* on a nickel-coated SUS 304 substrate.
Figure 9C:
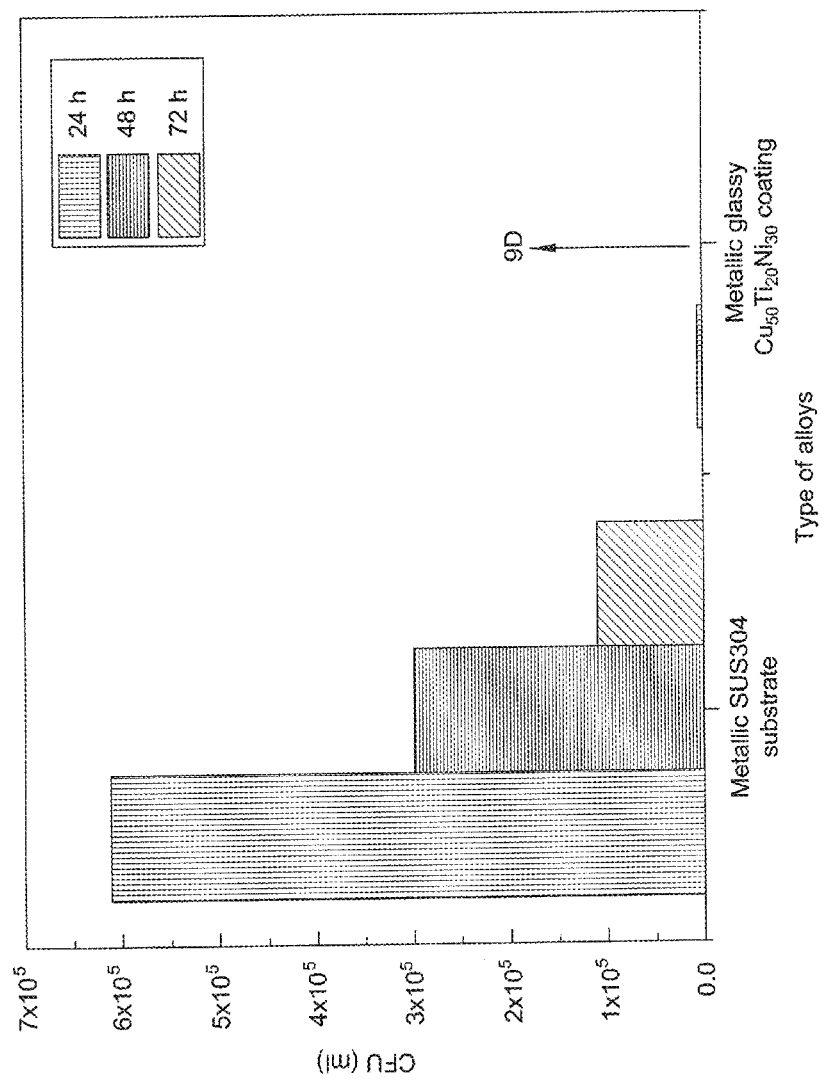
FIG. 9C is a chart showing biofilm formation by *E. coli* on an uncoated SUS 304 substrate.
Figure 9D:
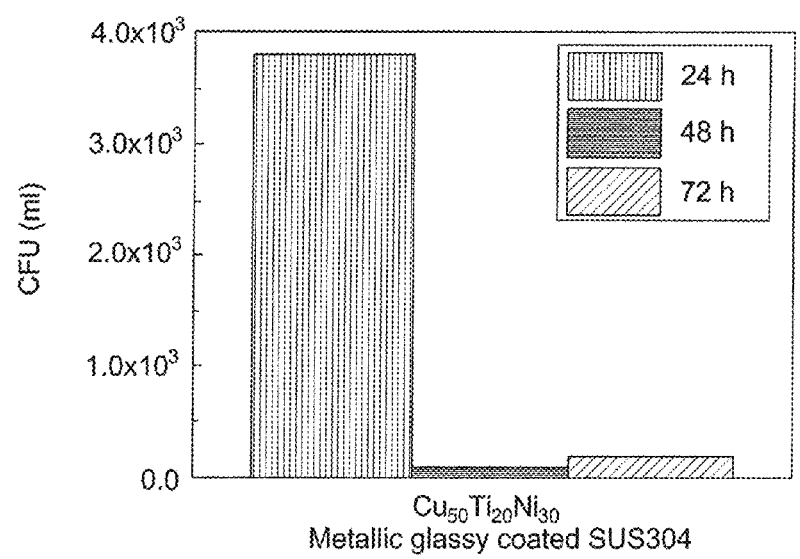
FIG. 9D is a chart showing biofilm formation by *E. coli* on a $Cu_{50}Ti_{20}Ni_{30}$ alloy-coated SUS 304 substrate.

The friction and wear behaviors of SUS304 substrate before and after cold spray coating with metallic glassy Cu$_{50}$Ti$_{20}$Ni$_{30}$ powders were investigated by a pin-on disc tribometer, using a WC—Ni composite ball. The variation of friction coefficients (COFs) measure for SUS304 and Cu$_{50}$Ti$_{20}$Ni$_{30}$ coating with sliding time at a total sliding distance of 100 m are presented in FIGS. 8(A) and 8(B) respectively. During the early stage of sliding time (25 s) the COFs for SUS304 and Cu-based coated sample were 0.51 and 0.14, respectively. Increasing the sliding time to 50 s led to increase the COFs for SUS304 and metallic glassy coated sample to the level of 0.70 and 0.33, respectively as shown in FIGS. 8A and 8B, respectively. Then, the COFs reached to 0.77 and 0.43 for SUS304 and Cu$_{50}$Ti$_{20}$Ni$_{30}$ coating, respectively. After 150 s of the sliding time, the COF for SUS304 saturated at 0.83 without any remarkable changes until the end of the testing time (FIG. 8A). The COF for Cu$_{50}$Ti$_{20}$Ni$_{30}$ coating sample, however, reached to a value of 48 during the sliding time ranged from 150 s to 500 s, as shown in FIG. 8B. The low COF value measured for the coating material can be attributed to its high nanohardness values (~3.1 GPa) comparing with the lower hardness (1.29 GPa) for the SUS304 substrate material.

During the last stage of the sliding time (500 s to 950 s) and toward the end of the test, the COF recorded for metallic glassy coating material exhibited a slight monotonical decreasing reached to about 0.45 after 950 s, as shown in FIG. 8B. This can be attributed to the dense random packed structure known for the amorphous structured metals and the uniformity in the chemical composition of the prepared powders together with the high hardness value recorded in the present study for the coating material. Such characteristics leading to a stable and low friction coefficient upon increasing the applied sliding time, as elucidated in FIG. 8B.

Basically, the coating material consisted of the alloying elements of Ni, Cu, and Ti. The large grains embedded at the metallic glassy coating layer surface in the shallow wear grooves were related by those shots released from the WC/Ni ball during the wear test. However, the microhardness of the ball (pin) used against the metallic glassy coated SUS304 (disk) has a high value of about 14.37 GPa (ASM International Handbook Committee 1990), it severely worn during the wear test. This is implying a high hardness values of the disk materials (metallic glassy coat) and its high resistance.

The FE-SEM micrograph of a selected zone taken from the groove e displays two individual zones with different elevations. The upper zone possessed large cracked grains morphology and consisted of WC/Ni composite, indicated by the x-ray elemental distribution. Moreover, small sized WC/Ni shots were embedded into the lower zone, as suggested by the x-ray elemental mapping. This lower zone is corresponding to the metallic glassy coated SUS304, as suggested by the elemental distribution of Ni. It showed be notified that a large volume fraction of the metallic glassy coating phase was existed under beneath the large-grained WC/Ni, as suggested by the presence of the alloying elements in X-ray mapping.

FIG. 9 shows the inhibitory effect of coated substrate against $E.$ $coli$ biofilm formation incubated for 24 h, 48 h and 72 h. High bacteria count was observed on the negative control substrate SUS304, only Cu coated substrate showed no growth as shown in FIG. 9A. Although the inhibitory effect of Cu on biofilm formation is not well known, it is thought that Cu ion released from Cu plays an important role in alter the protein structure of bacterial cell wall.

Figure 7B:
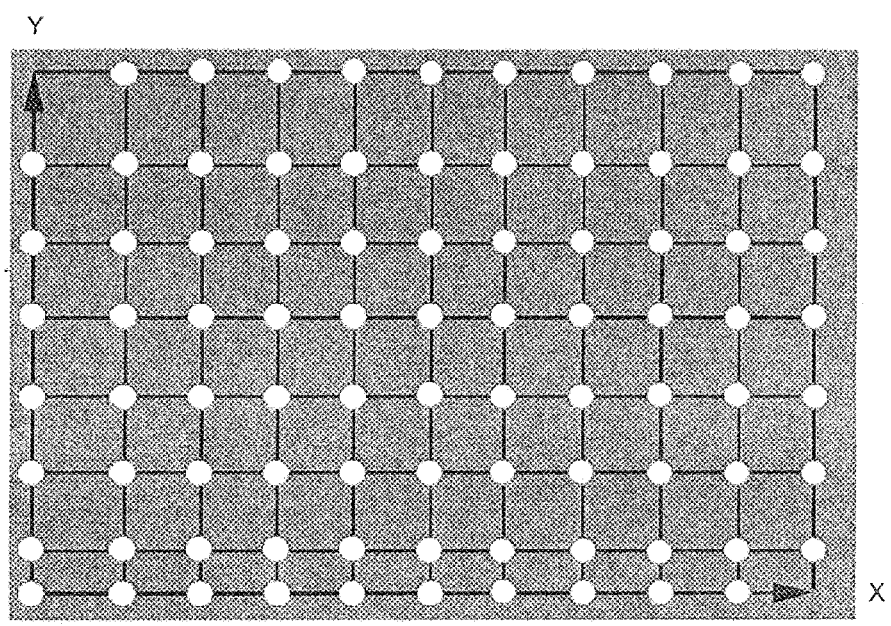
FIG. 7B is a diagram of the area 7B of FIG. 7A.
Figure 7C:
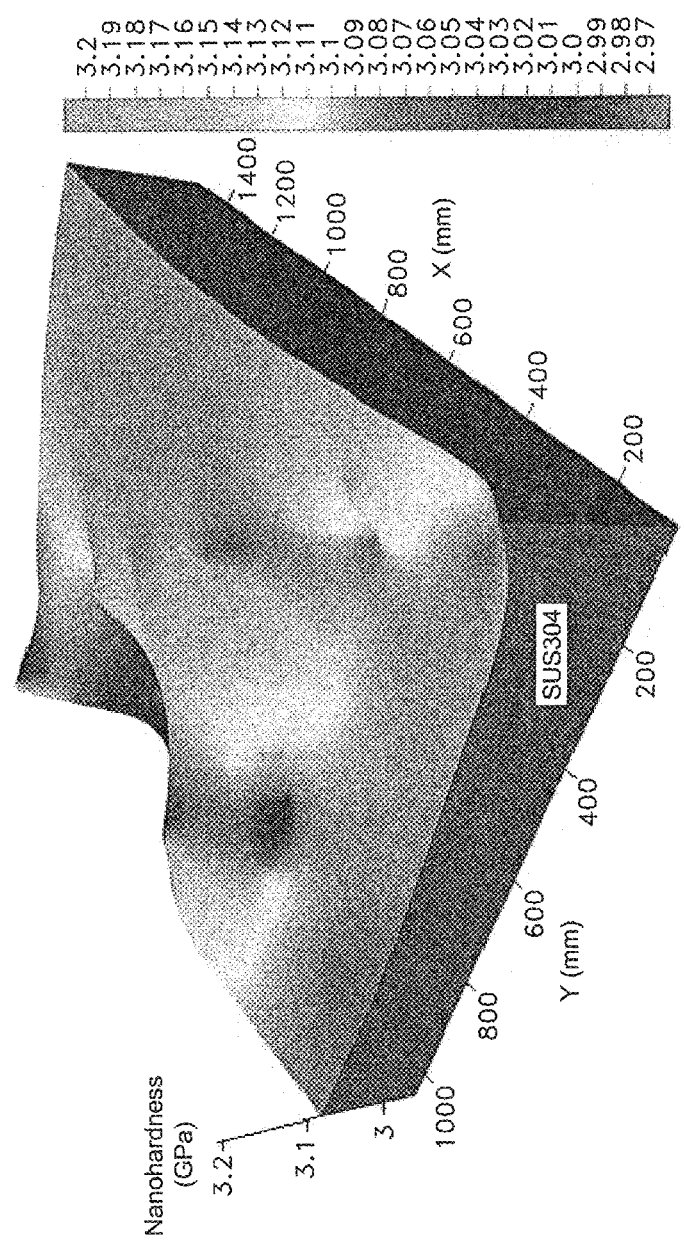
FIGS. 7C and 7D are three-dimensional graphs showing the corresponding nanohardness and Young's modulus results of the coating of FIG. 7A.
Figure 7D:
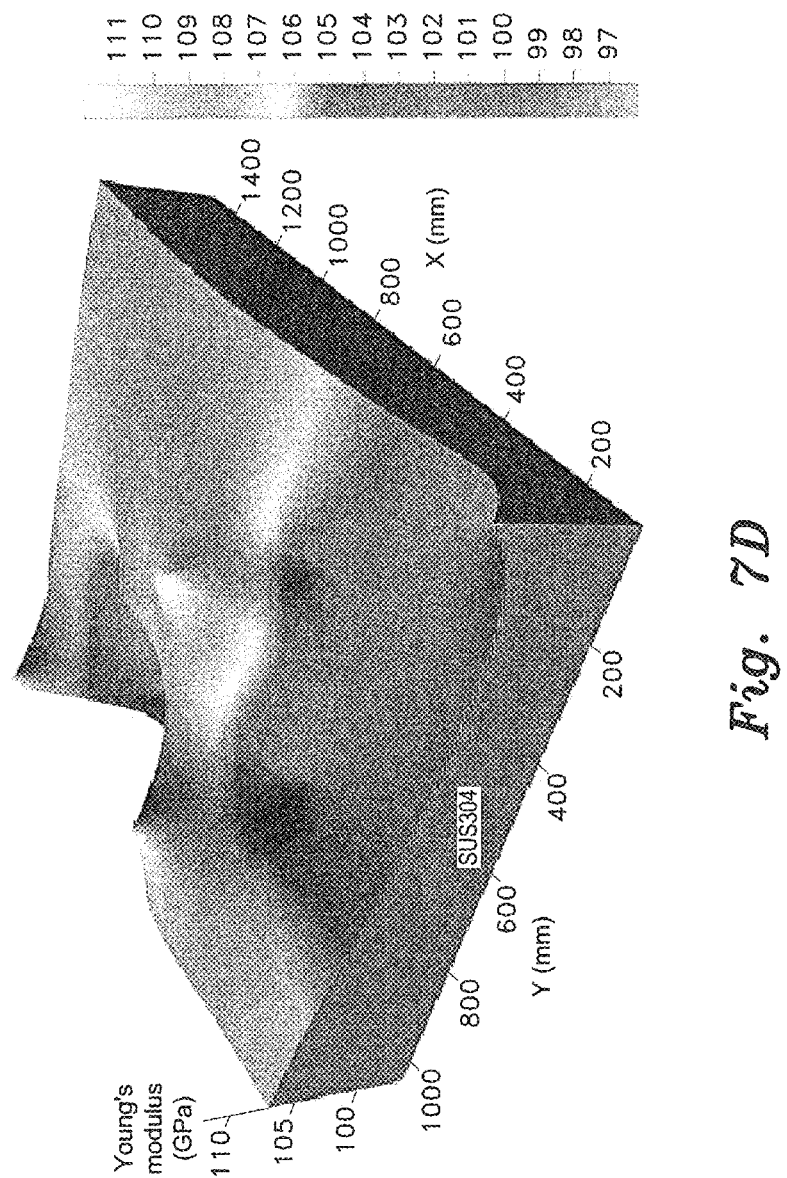

The substrates coated with $Cu_{50}Ti_{20}Ni_{30}$ remarkably inhibited colony formation of $E.$ $coli$ compared with SUS304 as shown in FIG. 7B. These results were statistically significant ($p<0.05$). Moreover, results suggest that $Cu_{50}Ti_{20}Ni_{30}$ coated materials will be very effective against biofilm formation in addition, results showed the improvement of anti-microbial effect of Ni when combined with Cu and Ti. It was reported that the antimicrobial effect of copper ions is dose-dependent.

It was found that the pure Cu-100% significantly decreased Biofilm formation. However, antimicrobial activity was also well obtained with only Cu-50%. This suggests synergic effect between Cu, Ti and Ni.

It would be apparent to those skilled in the art that several conclusions would follow naturally from the foregoing results. A metastable phase of metallic glassy Cu50Ti20Ni30 alloy powders was obtained upon low-energy ball milling the elemental metal powders for 100 h. The powder particle size of the obtained metallic glassy alloys had an average particle size of 1.7 microns in diameter with spherical-like morphology.

This solid amorphous alloy transforms into a liquid glassy phase at a glass transition temperature of 358.3° C. However, the glassy phase was no longer existed when the powders heated in a DSC and tended to transform into $Ti_2Cu$ and $CuTiNi_2$ ordered phases at 419.3° C. and 447.5° C., respectively. The total enthalpy change of crystallization was calculated and found to be −4.8 kJ/mol. The fabricated metallic glassy ternary alloy exhibited a wide supercooled liquid region of 61° C.

Based on the purpose of the present invention, the homogeneous synthetics $Cu_{50}Ti_{20}Ni_{30}$ alloy powders obtained after 100 h of ball milling were employed for performing double-face coating of SUS304 sheet, using cold spraying technique processed at 400° C. under helium gas atmospheric pressure. This advanced coating technique did not lead to crystallize the metallic glassy phase, resulted the formation of uniform coating layers with a thickness of about 10 microns.

The $Cu_{50}Ti_{20}Ni_{30}$ metallic glassy coated SUS304 extraordinary high nano-hardness value (3.1 GPa) and showed a low value of the coefficient of friction ranging from 0.45 to 0.45. This invention shows that the inhibition of bacterial biofilm by $Cu_{50}Ti_{20}Ni_{30}$ can offer a viable possibility for controlling biofilm formation.

Additionally, nano-manufacturing of antibacterial and antimicrobial surface protective coating that can be used for food sector, Medial applications. In contrast to the other reported methods and materials currently used for the sample target, the method enjoys the following advantages: Starting materials are commercial powders available in the market; Synthesizing of the metallic glassy powders is achieved at room temperature, the coating process is conducted at low temperature (400° C.). This method of using cold spray technology is an environmental friendly process that is able to offer tough, hard metallic glassy coating materials with any thickness and any desired area. The material and process can be employed on-site outdoor.

It is to be understood that the present invention is not limited to the embodiments described above, but encompasses any and all embodiments within the scope of the following claims.

We claim:

1. A method of applying metallic glassy alloy powders to a substrate as an antimicrobial coating, comprising the steps of:
providing a mechanically alloyed mixture of copper, titanium and nickel, wherein the mechanically alloyed mixture comprises a metallic, glassy powder of amorphous $Cu_{50}Ti_{20}Ni_{30}$; and
applying a uniform coating of the powder to the substrate by cold spraying.

2. A method for coating a substrate with metallic glassy powder, comprising the steps of:
providing a dry substrate having a surface to be coated;
synthesizing metallic alloy glassy powders, wherein the synthesis includes:
i) disposing metal powders in a ball-milling container, the ball milling container including a plurality of milling balls and having an inert atmosphere therein;
ii) disposing the ball-milling container including the metal powders in a ball mill; and
iii) operating the ball mill for a period of time to achieve high-energy collision of the plurality of balls with the metal powders in the container, the high energy collision producing a glassy metallic alloy powder, wherein the alloyed powder comprises amorphous $Cu_{50}Ti_{20}Ni_{30}$;
charging the metallic glassy powders in a cold spray feeder; and
spraying the metallic glassy powders on to the surface in a supersonic jet of inert gas at a flow velocity of at least 1200 m/s, thereby coating the surface of the substrate with said metallic glassy powder.

3. The method for coating a substrate according to claim 2, wherein the step of spraying is repeated at least five times.

4. The method for coating a substrate according to claim 2, wherein the step of spraying comprises spraying at a temperature of 400° C.

5. The method for coating a substrate according to claim 2, wherein the substrate comprises a sheet of stainless steel.

6. The method for coating a substrate according to claim 2, wherein the coating comprises a uniform coating having a thickness of at least about 10 microns.

7. The method for coating a substrate according to claim 2, further comprising the step of is pre-cleaning the substrate by alumina blasting at room temperature.

8. The method for coating a substrate according to claim 2, wherein the step of synthesizing metallic alloy glassy powders occurred at an onset temperature of 358.3° C. which constitutes the glass transition temperature ($T_g$) and defines an endothermic reaction.

\* \* \* \* \*